United States Patent
Zhang et al.

(10) Patent No.: US 10,964,224 B1
(45) Date of Patent: Mar. 30, 2021

(54) GENERATING SCORES AND FEEDBACK FOR WRITING ASSESSMENT AND INSTRUCTION USING ELECTRONIC PROCESS LOGS

(71) Applicant: Educational Testing Service, Princeton, NJ (US)

(72) Inventors: Mo Zhang, Plainsboro, NJ (US); Jiangang Hao, Princeton, NJ (US); Paul Deane, Lawrenceville, NJ (US)

(73) Assignee: Educational Testing Service, Princeton, NJ (US)

( * ) Notice: Subject to any disclaimer, the term of this patent is extended or adjusted under 35 U.S.C. 154(b) by 529 days.

(21) Appl. No.: 15/456,874

(22) Filed: Mar. 13, 2017

Related U.S. Application Data

(60) Provisional application No. 62/308,255, filed on Mar. 15, 2016.

(51) Int. Cl.
  *G09B 7/02* (2006.01)
  *G09B 5/02* (2006.01)
  (Continued)

(52) U.S. Cl.
  CPC ............... *G09B 7/02* (2013.01); *G09B 5/02* (2013.01); *G09B 5/14* (2013.01); *A61B 5/16* (2013.01);
  (Continued)

(58) Field of Classification Search
  CPC .......... G09B 7/00; G09B 7/02; G09B 19/025; G09B 7/08; G09B 5/02; G09B 5/14; A61B 5/16; A61B 5/162
  See application file for complete search history.

(56) References Cited

U.S. PATENT DOCUMENTS 6,113,393 A * 9/2000 Neuhaus ............... G09B 17/006
  434/156
6,181,909 B1 1/2001 Burstein et al.
  (Continued)

OTHER PUBLICATIONS

Almond, Russell, Deane, Paul, Quinlan, Thomas, Wagner, Michael, Sydorenko, Tetyana; A Preliminary Analysis of Keystroke Log Data From a Timed Writing Task; Educational Testing Service, Research Report RR-12-23; Nov. 2012.
  (Continued)

*Primary Examiner* — Jack Yip
(74) *Attorney, Agent, or Firm* — Jones Day

(57) ABSTRACT

Systems and methods are provided for providing feedback on a user's writing behavior in generating a constructed response. An electronic process log for the constructed response is received. The electronic process log is processed to generate a vector having a predetermined number of elements. The vector comprises information related to the user's actions in generating the constructed response and includes (i) data indicating types of actions performed by the user in generating the constructed response, (ii) time points associated with the actions, and (iii) locations associated with the actions, each location indicating whether an associated action occurred within a word, between words, within a phrase, between phrases, within a sentence, between sentences, within a paragraph, or between paragraph. The vector is compared to one or more vectors associated with other constructed responses, and feedback is generated based on the comparison.

19 Claims, 14 Drawing Sheets

(51) Int. Cl.
*G09B 5/14* (2006.01)
*A61B 5/16* (2006.01)
*G09B 19/02* (2006.01)
*G09B 7/08* (2006.01)
*G09B 7/00* (2006.01)

(52) U.S. Cl.
CPC ............... *A61B 5/162* (2013.01); *G09B 7/00* (2013.01); *G09B 7/08* (2013.01); *G09B 19/025* (2013.01)

(56) References Cited

U.S. PATENT DOCUMENTS

| | | | |
|---|---|---|---|
| 6,366,759 B1 | 4/2002 | Burstein et al. | |
| 6,755,657 B1* | 6/2004 | Wasowicz | G09B 5/04 434/167 |
| 2001/0014440 A1* | 8/2001 | Oyama | G09B 13/00 434/227 |
| 2004/0140957 A1* | 7/2004 | Casey | G06F 3/0202 345/168 |
| 2005/0027523 A1* | 2/2005 | Tarlton | G10L 15/22 704/234 |
| 2006/0074659 A1* | 4/2006 | Adams | G09B 5/04 704/251 |
| 2007/0248938 A1* | 10/2007 | Ronald | G09B 5/06 434/178 |
| 2009/0190839 A1* | 7/2009 | Higgins | G06F 16/3347 382/209 |
| 2010/0159433 A1* | 6/2010 | Graham | G09B 7/00 434/353 |
| 2012/0088222 A1* | 4/2012 | Considine | G09B 7/02 434/362 |
| 2012/0221895 A1* | 8/2012 | Mollicone | G06Q 30/02 714/32 |
| 2012/0278022 A1* | 11/2012 | Kan | A61B 5/7221 702/85 |
| 2013/0157235 A1* | 6/2013 | Ellsworth, Jr. | G09B 13/04 434/227 |
| 2013/0227402 A1* | 8/2013 | Rossen-Knill | G06F 11/3438 715/255 |
| 2014/0279763 A1* | 9/2014 | Madnani | G06Q 10/10 706/12 |
| 2014/0342341 A1* | 11/2014 | Rea | G09B 7/02 434/351 |
| 2015/0294579 A1* | 10/2015 | Rudolph | G09B 7/00 434/353 |
| 2016/0133147 A1* | 5/2016 | Deane | G09B 7/02 434/353 |
| 2016/0140453 A1* | 5/2016 | Adderly | G06N 5/022 706/11 |
| 2016/0379513 A1* | 12/2016 | DuQuette | G09B 5/065 434/227 |

OTHER PUBLICATIONS

Alves, Rui Alexandre, Castro, Sao Luis, De Sousa, Liliana, Stromqvist, Sven; Influence of Typing Skill on Pause-Execution Cycles in Written Composition; Ch. 4 in Writing in Cognition: Research and Applications (Studies in Writing, vol. 20), G. Rijlaarsdam (Ed.); pp. 55-65; Elsevier, Amsterdam; 2007.
Baaijen, Veerle, Galbraith, David, De Glopper, Kees; Keystroke Analysis: Reflections on Procedures and Measures; Written Communication, 29(3); pp. 246-277; Jul. 2012.
Banerjee, Ritwik, Feng, Song, Kang, Jun, Choi, Yejin; Keystroke Patterns as Prosody in Digital Writings: A Case Study with Deceptive Reviews and Essays; Proceedings of the 2014 Conference on Empirical Methods in Natural Language Processing; 2014.
Beauvais, Caroline, Olive, Thierry, Passerault, Jean-Michel; Why Are Some Texts Good and Others Not? Relationship Between Text Quality and Management of the Writing Processes; Journal of Educational Psychology, 103(2); pp. 415-428; 2011.

Bennett, Randy Elliot; Cognitively Based Assessment of, for, and as Learning (CBAL): A Preliminary Theory of Action for Summative and Formative Assessment; Measurement, 8; pp. 70-91; 2010.
Chenoweth, N. Ann, Hayes, John; Fluency in Writing: Generating Text in L1 and L2; Written Communication, 18(1); pp. 80-98; Jan. 2001.
Chukharev-Hudilainen, Evgeny; Pauses in Spontaneous Written Communication: A Keystroke Logging Study; Journal of Writing Research, 6(1); pp. 61-84; 2014.
Cohen, Jacob; Weighted Kappa: Nominal Scale Agreement with Provision for Scaled Disagreement or Partial Credit; Psychological Bulletin, 70(4); pp. 213-220; Oct. 1968.
Deane, Paul; Using Writing Process and Product Features to Assess Writing Quality and Explore How Those Features Relate to Other Literacy Tasks; Educational Testing Service, Research Report RR-14-03; Jun. 2014.
Deane, Paul, Sabatini, John, Feng, Gary, Sparks, Jesse, Song, Yi, Fowles, Mary, O'Reilly, Tenaha, Jueds, Katherine, Krovetz, Robert, Foley, Colleen; Key Practices in the English Language Arts (ELA): Linking Learning Theory, Assessment, and Instruction; Educational Testing Service, Research Report RR-15-17; Dec. 2015.
Deane, Paul, Zhang, Mo; Exploring the Feasibility of Using Writing Process Features to Assess Text Production Skills; Educational Testing Service, Research Report RR-15-26; Dec. 2015.
Dragsted, Barbara, Carl, Michael; Towards a Classification of Translation Styles Based on Eye-Tracking and Keylogging Data; Journal of Writing Research, 5(1); pp. 133-158; 2013.
Fleiss, Joseph, Cohen, Jacob; The Equivalence of Weighted Kappa and the Intraclass Correlation Coefficient as Measures of Reliability; Educational and Psychological Measurement, 33; pp. 613-619; 1973.
Gould, John; Experiments on Composing Letters: Some Facts, Some Myths, and Some Observations; in Cognitive Processes in Writing, Ch. 5 in L. Gregg & E. Steinberg (Eds.); Lawrence Erlbaum: Hillsdale, NJ; pp. 97-127; 1980.
Grabowski, Joachim; The Internal Structure of University Students' Keyboard Skills; Journal of Writing Research, 1(1); pp. 27-52; 2008.
Hao, Jiangang, Smith, Lawrence, Mislevy, Robert, Von Davier, Alina, Bauer, Malcolm; Taming Log Files From Game/Simulation-Based Assessments: Data Models and Data Analysis Tools; Educational Testing Service, Research Report RR-16-10; Jun. 2016.
Hinkle, Dennis, Wiersma, William, Jurs, Stephen; Applied Statistics for the Behavioral Sciences, 5th Ed.; Haughton Mifflin Company: Boston, MA; 2003.
Johnson, Stephen; Hierarchical Clustering Schemes; Psychometrika, 32(3); pp. 241-254; Sep. 1967.
Jones, Eric, Oliphant, Travis, Peterson, Pearu; SciPy: Open Source Scientific Tools for Python [Computer Software]; http://www.scipy.org/; 2014.
Kalbfleisch, John, Prentice, Ross; The Statistical Analysis of Failure Time Data, 2nd Ed.; John Wiley and Sons: Hoboken, NJ; 2002.
Leijten, Marielle, Macken, Lieve, Hoste, Veronique, Van Horenbeeck, Eric, Van Waes, Luuk; From Character to Word Level: Enabling the Linguistic Analyses of Inputlog Process Data; Proceedings of the EACL 2012 Workshop on Computational Linguistics and Writing; pp. 1-8; Apr. 2012.
LEIJTEN, Marielle, Van Waes, Luuk; Keystroke Logging in Writing Research: Using Inputlog to Analyze and Visualize Writing Processes; Written Communication, 30(3); pp. 358-392; Jul. 2013.
Leijten, Marielle, Van Waes, Luuk, Schriver, Karen, Hayes, John; Writing in the Workplace: Constructing Documents Using Multiple Digital Sources; Journal of Writing Research, 5(3); pp. 285-337; 2014.
Miller, Kristyan; Academic Writers On-line: Investigating Pausing in the Production of Text; Language Teaching Research, 4(2); pp. 123-148; Apr. 2000.
Roca De Larios, Julio, Manchon, Rosa, Murphy, Liz, Marin, Javier; The Foreign Language Writer's Strategic Behaviour in the Allocation of Time to Writing Processes; Journal of Second Language Writing, 17(1); pp. 30-47; Mar. 2008.

(56) References Cited

OTHER PUBLICATIONS

Ulrich, Rolf, Miller, Jeff; Information Processing Models Generating Lognormally Distributed Reaction Times; Journal of Mathematical Psychology, 37(4); pp. 513-525; Dec. 1993.

Van Der Linden, Wim; A Lognormal Model for Response Times on Test Items; Journal of Educational and Behavioral Statistics, 31(2); pp. 181-204; Summer 2006.

Van Waes, Luuk, Leijten, Marielle, Van Weijen, Daphne; Keystroke Logging in Writing Research: Observing Writing Processes with Inputlog; GFI-Journal, 2-3; pp. 41-64; 2009.

Xu, Cuiqin, Ding, Yanren; An Exploratory Study of Pauses in Computer-Assisted EFL Writing; Language Learning & Technology, 18(3); pp. 80-96; Oct. 2014.

Zhang, Mo, Deane, Paul; Process Features in Writing: Internal Structure and Incremental Value Over Product Features; Educational Testing Service, Research Report RR-15-27; Dec. 2015.

\* cited by examiner

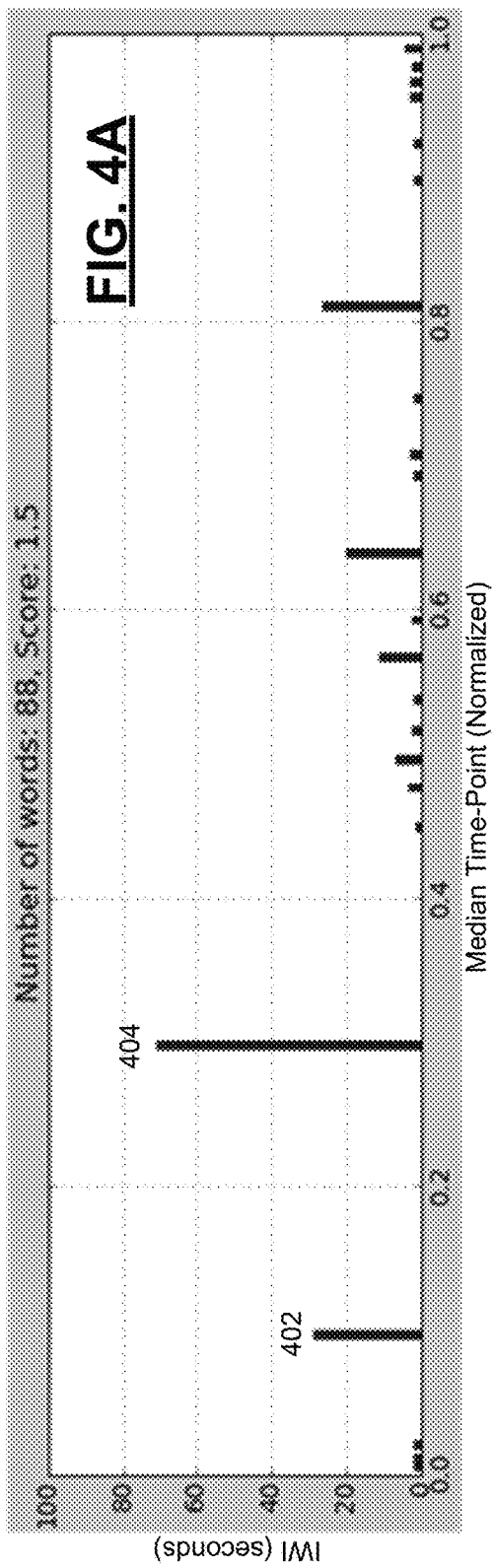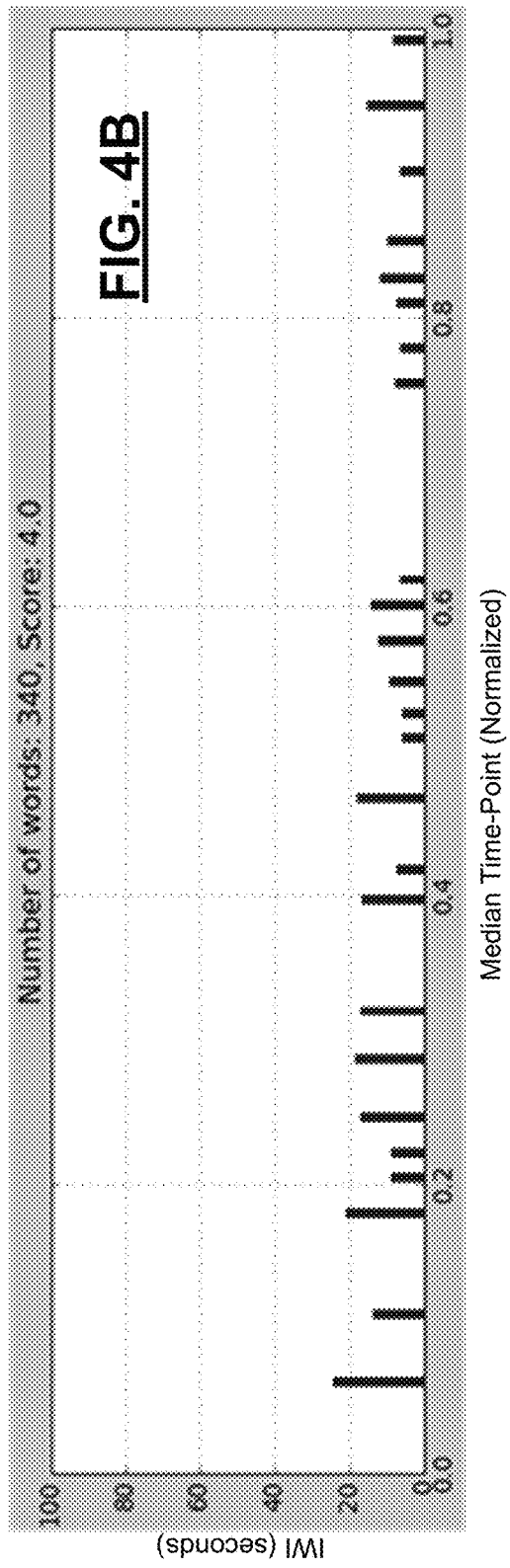

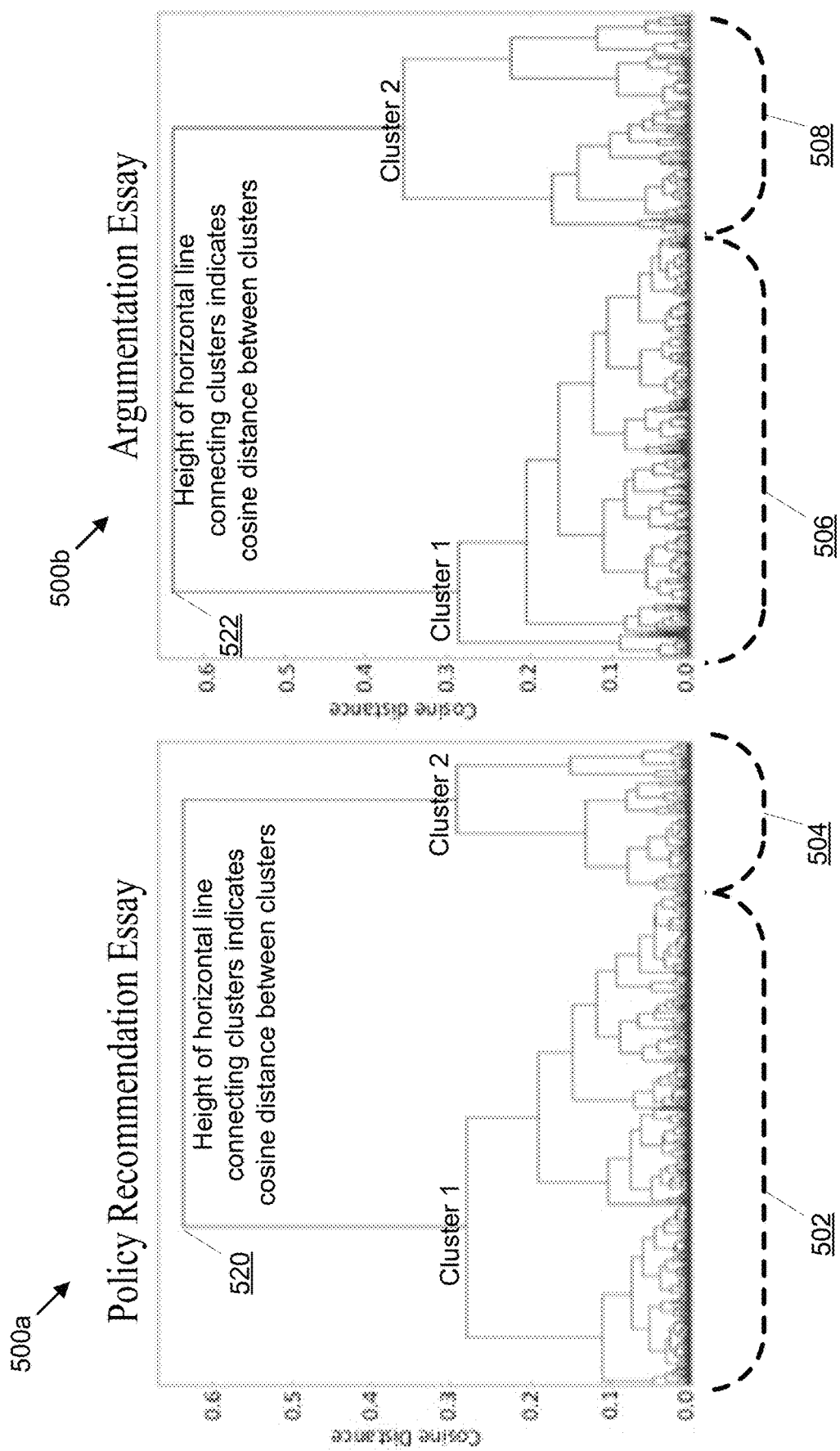

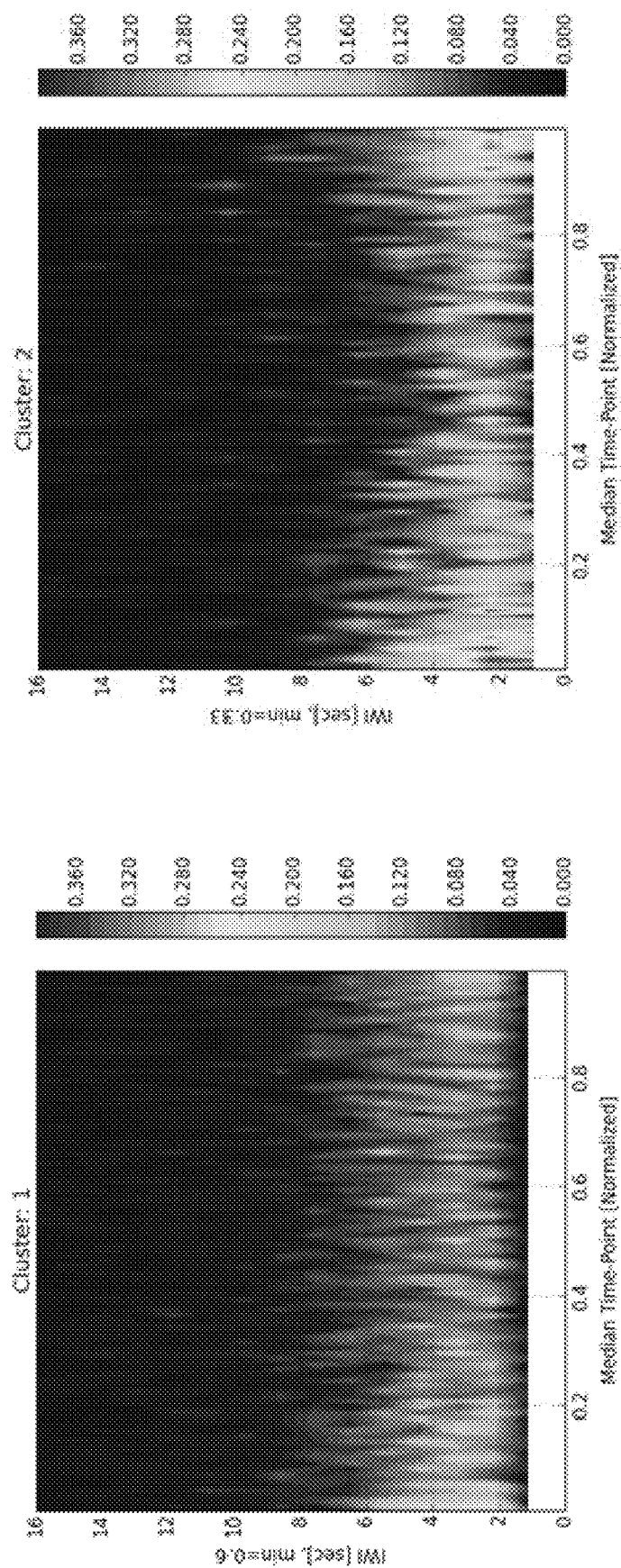

| Policy Recommendation Essay | | | | |
|---|---|---|---|---|
| Cluster | N | Human Score Mean(SD) | Word Insert Mean(SD) | Writing Time Mean(SD) |
| 1 | 635 | 2.58 (0.80) | 230 (123) | 459 (239) |
| 2 | 196 | 2.27 (0.81) | 181 (111) | 382 (247) |
| Effect Size | | ES = 0.39 | ES = 0.49 | ES = 0.37 |
| t-value | | 4.73 ($p < 0.0001$) | 5.99 ($p < 0.0001$) | 4.59 ($p < 0.0001$) |

| Argumentation Essay | | | | |
|---|---|---|---|---|
| Cluster | N | Human Score Mean(SD) | Word Insert Mean(SD) | Writing Time Mean(SD) |
| 1 | 591 | 2.87 (0.85) | 233 (110) | 353 (203) |
| 2 | 311 | 2.57 (0.90) | 178 (97) | 293 (189) |
| Effect Size | | ES = 0.35 | ES = 0.57 | ES = 0.32 |
| t-value | | 4.94 ($p < 0.0001$) | 8.10 ($p < 0.0001$) | 4.54 ($p < 0.0001$) |

FIG. 10a

GENERATING SCORES AND FEEDBACK FOR WRITING ASSESSMENT AND INSTRUCTION USING ELECTRONIC PROCESS LOGS

CROSS-REFERENCE TO RELATED APPLICATIONS

The present application claims priority to U.S. Provisional Application Ser. No. 62/308,255, entitled "Generating Scores and Feedback for Writing Assessment and Instruction Using Electronic Process Logs," filed Mar. 15, 2016.

FIELD

This disclosure is related generally to automated test response evaluation and more particularly to utilization of process metrics in determining an automated score or providing feedback on a user's writing behavior, proficiency, or practice.

BACKGROUND

Students are tested for a variety of purposes (e.g., to determine students' understanding of a concept, vocabulary knowledge, etc.). One method of testing students utilizes test questions that require a constructed response. Examples of constructed responses include free-form, non-multiple choice responses such as essays, spoken responses, or show-your-work math responses. Conventionally, one or more human graders review students' constructed responses and manually assign scores to the constructed responses. The one or more human graders may also provide feedback on the constructed responses, in addition to the scores. The graders' evaluation and feedback thus focuses on the final written products produced by the students (i.e., the constructed responses in their final, submitted form). Automated scoring systems have been developed for evaluating students' constructed responses. Similar to the aforementioned manual scoring methods, the automated scoring systems are configured to score the final written products produced by the students and/or provide feedback on the final written products.

SUMMARY

Systems and methods are provided for providing feedback on a user's writing behavior in generating a constructed response. In an example computer-implemented method, an electronic process log for the constructed response is received. The electronic process log comprises a plurality of time-stamped entries, each of the entries being associated with a keystroke made by the user in generating the constructed response and indicating a change in text of the constructed response due to the keystroke. The electronic process log is processed to generate a vector having a predetermined number of elements. The vector comprises information related to the user's actions in generating the constructed response and includes (i) data indicating types of actions (e.g., pauses, insertions, deletions, jumping actions, pasting actions, etc.) performed by the user in generating the constructed response, (ii) time points associated with the actions, each time point indicating a point in time in the composition process at which an associated action occurred, (iii) locations associated with the actions, each location indicating, for example, whether an associated action occurred within a word, between words, within a phrase, between phrases, within a sentence, between sentences, within a paragraph, or between paragraph, and in various embodiments (iv) duration of the action in terms of the time elapsed or text length. The vector is processed to generate feedback on the user's actions in generating the constructed response. The processing includes comparing the vector to one or more vectors associated with other constructed responses and generating the feedback based on the comparison. In embodiments, the types of actions include pauses, and the vector further includes durations of time indicating how long the user paused between typing adjacent words, letters, phrases, sentences, or paragraphs of the constructed response.

An example system for providing feedback on a user's writing behavior in generating a constructed response includes a processing system and computer-readable memory in communication with the processing system encoded with instructions for commanding the processing system to execute steps. In executing the steps, an electronic process log for the constructed response is received. The electronic process log comprises a plurality of time-stamped entries, each of the entries being associated with a keystroke made by the user in generating the constructed response and indicating a change in text of the constructed response due to the keystroke. The electronic process log is processed to generate a vector having a predetermined number of elements. The vector comprises information related to the user's actions in generating the constructed response and includes (i) data indicating types of actions (e.g., pauses, insertions, deletions, jumping actions, pasting actions, etc.) performed by the user in generating the constructed response, (ii) time points associated with the actions, each time point indicating a point in time in the composition process at which an associated action occurred, (iii) locations associated with the actions, each location indicating, for example, whether an associated action occurred within a word, between words, within a phrase, between phrases, within a sentence, between sentences, within a paragraph, or between paragraph, and in various embodiments (iv) duration of the action in terms of the time elapsed or text length. The vector is processed to generate feedback on the user's actions in generating the constructed response. The processing includes comparing the vector to one or more vectors associated with other constructed responses and generating the feedback based on the comparison. In embodiments, the types of actions include pauses, and the vector further includes durations of time indicating how long the user paused between typing adjacent words, letters, phrases, sentences, or paragraphs of the constructed response.

An example non-transitory computer-readable storage medium for providing feedback on a user's writing behavior in generating a constructed response comprises computer executable instructions which, when executed, cause a processing system to execute steps. In executing the steps, an electronic process log for the constructed response is received. The electronic process log comprises a plurality of time-stamped entries, each of the entries being associated with a keystroke made by the user in generating the constructed response and indicating a change in text of the constructed response due to the keystroke. The electronic process log is processed to generate a vector having a predetermined number of elements. The vector may comprise information related to the user's actions in generating the constructed response and includes (i) data indicating types of actions (e.g., pauses, insertions, deletions, jumping actions, pasting actions, etc.) performed by the user in generating the constructed response, (ii) time points associated with the actions, each time point indicating a point in time in the composition process at which an associated action occurred, (iii) locations associated with the actions, each location indicating, for example, whether an associated action occurred within a word, between words, within a phrase, between phrases, within a sentence, between sentences, within a paragraph, or between paragraph, and in various embodiments (iv) duration of the action in terms of the time elapsed or text length. The vector is processed to generate feedback on the user's actions in generating the constructed response. The processing includes comparing the vector to one or more vectors associated with other constructed responses and generating the feedback based on the comparison. In embodiments, the types of actions include pauses, and the vector further includes durations of time indicating how long the user paused between typing adjacent words, letters, phrases, sentences, or paragraphs of the constructed response.

BRIEF DESCRIPTION OF THE DRAWINGS

FIG. 4A illustrates an exemplary analysis of process log data in accordance with disclosed embodiments;

FIG. 4B illustrates an exemplary analysis of process log data in accordance with disclosed embodiments;

FIG. 5A illustrates an exemplary analysis based on process log data in accordance with disclosed embodiments;

FIG. 5B illustrates an exemplary analysis based on process log data in accordance with disclosed embodiments;

FIG. 8A illustrates an exemplary clustering analysis based on process log data in accordance with disclosed embodiments;

FIG. 8B illustrates an exemplary clustering analysis based on process log data in accordance with disclosed embodiments;

FIG. 10a illustrates an exemplary vector data based on process log data in accordance with disclosed embodiments;

DETAILED DESCRIPTION

Figure 1:
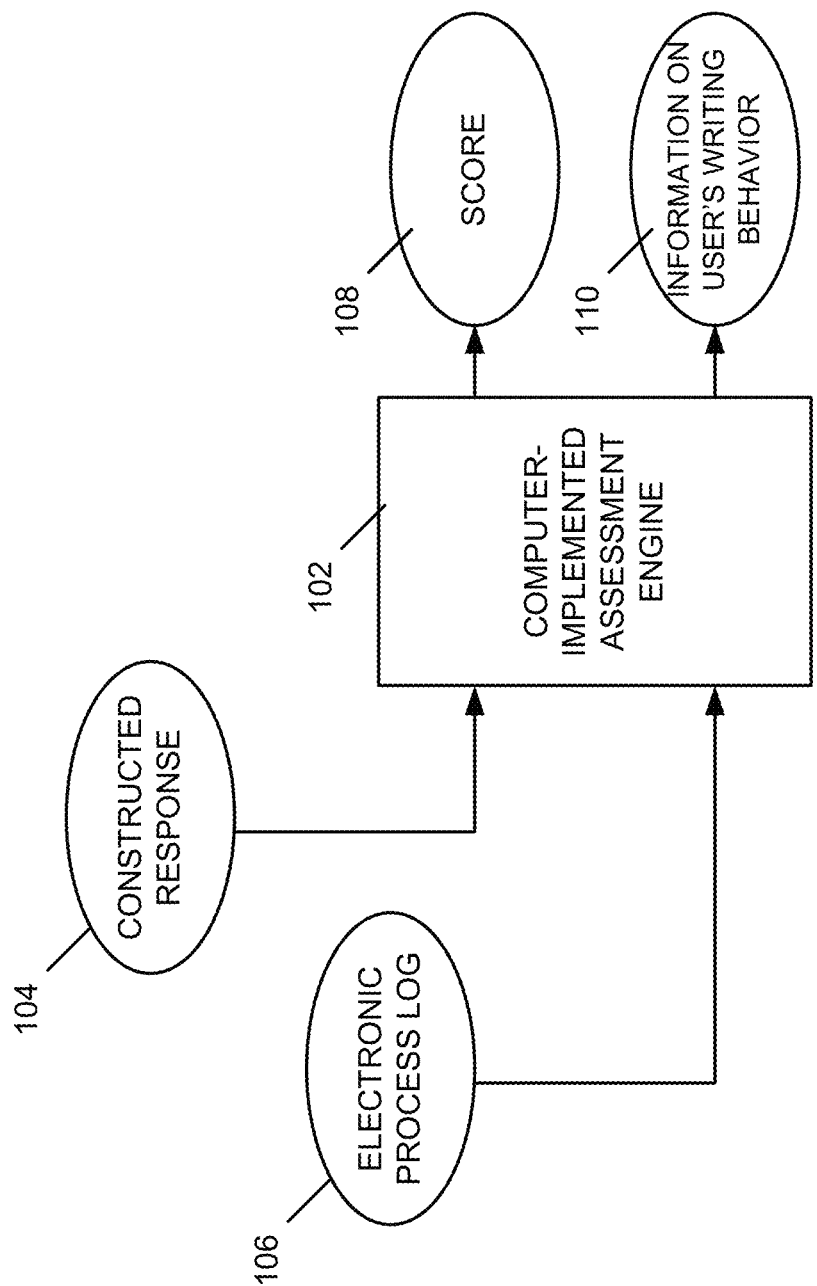
FIG. 1 is a block diagram of an example system for automatically scoring a constructed response in accordance with disclosed embodiments.

The instant disclosure provides systems and methods for providing feedback on a user's writing behavior in generating a constructed response. In embodiments described below, an electronic process log including data indicative of writing processes utilized by the user in generating the constructed response is processed. By processing the electronic process log, a vector is generated, where the vector includes information related to the user's actions in generating the constructed response.

Although examples described below utilize vectors storing information on the user's pauses (i.e., the user's pauses between typing adjacent letters, words, sentences, phrases, etc.), it should be appreciated that the vectors can store information on numerous other user actions. Such actions include, for example, insertion actions, deletion actions, jumping actions, copying actions, and pasting actions, among others. Thus, in examples, the vector includes (i) data indicating types of actions performed by the user (e.g., pauses, deletions, insertions, copying, pasting, jumping, etc.), (ii) time points associated with the actions (e.g., points in time in composition process at which the actions occurred), (iii) locations associated with the actions (e.g., indicating, for example, whether the actions occurred within a word, between words, within a phrase, between phrases, within a sentence, between sentences, within a paragraph, or between paragraph, etc.), and in various embodiments (iv) duration of the action in terms of the time elapsed or text length. When for example the action is a "pause," the vector may further include durations of time indicating how long the user paused between typing adjacent words, letters, phrases, sentences, or paragraphs of the constructed response. Alternatively, instead of a pause, a duration of an action may be measured a key depression (e.g. holding down the delete key), or the duration may be a count of key depressions (e.g. number of times a delete key was pressed), or a combination of a count and a time duration (e.g. number of times a delete key was pressed within a measured period of time).

As described below, the vector that is generated for a constructed response has a predetermined number of elements. By limiting the size of the vector to this predetermined number of elements, vectors for different constructed responses may be compared, despite differences in (i) the amounts of time users spent in generating the constructed responses, and (ii) the number of words in each of the constructed responses. Thus, by limiting the size of the vector as described herein, the vector can be compared with other vectors associated with other constructed response, and feedback can be generated based on the comparisons. Such feedback may provide information that classifies writing processes or writing styles employed by the users, among other information.

In U.S. application Ser. No. 14/937,164, filed on Nov. 10, 2015 and titled "Generating Scores and Feedback for Writing Assessment and Instruction Using Electronic Process Logs" systems and methods were described in the field of: providing automated test response evaluation based on process metrics useful for automated scoring based on a user's writing behavior, proficiency, or practice; and providing automated test response evaluation based on process metrics useful for automatically generating meaningful feedback on a user's writing behavior, proficiency, or practice. These systems and methods describe automatically generating an assessment of an evaluation response, where an assessment includes a score or feedback. For example, a disclosed method receives a response and an associated process log including information describing how a response was constructed or prepared (e.g., a description of the temporal evolution of the response). The response is evaluated on its own merits, and a value is generated that represents aspects of the response. The process log is processed in order to generate additional feature values related to the user's actions in generating the response. A score and/or feedback and/or information may then be generated based on the value representing aspects of the response and the additional feature values. The score can be based on weighted variables that are themselves generated based on training a scoring module with training texts. The assessment may further be based on the values or feature values satisfying a rule or condition (e.g. when a rule or condition is satisfied specific feedback is included in the response, or the score is affected in a deterministic fashion). The above mentioned U.S. application Ser. No. 14/937,164, filed on Nov. 10, 2015, is hereby incorporated by reference in its entirety as if fully set forth herein.

FIG. 1 is a block diagram of an example system for automatically scoring a constructed response 104 generated by a user and providing information on the user's writing behavior. In an example, the constructed response 104 is a textual response that is generated by the user in response to a given item (e.g., a test question, task, evaluation, prompt, request for information, application, etc.). In generating the constructed response 104, the user uses a keyboard. The keyboard may be a hardware keyboard (e.g., a hardware keyboard used with a desktop or laptop computer, smartphone, personal digital assistant (PDA), etc.) or a software keyboard (e.g., an on-screen keyboard that utilizes a touchscreen, mouse, or other input device to operate virtual keys). The user may use other input devices, along with the keyboard, in generating the constructed response 104. For example, the user may use a mouse to move a position of a cursor in an input text box, or may enter text or other responsive information or data or pictures using a stylus or any other input method. In embodiments, a response is generated manually, under observation by one or more sensors, and scanned into a data processor. The given item may include an open-ended question that requests a free-form, non-multiple choice response from the user. The given item may include a prompt that requests that the user generate a constructed response that is a short answer (e.g., a single word or phrase not comprising a complete sentence), one or more complete sentences, and/or an essay (e.g., comprising multiple sentences and/or paragraphs). The given item may be used in assessing various attributes of the user (e.g., the user's reading comprehension, the user's understanding of a concept, the user's vocabulary knowledge, writing proficiency, etc.). In examples, the user is a human that generates the constructed response 104, in other examples the user is a machine based intelligence being evaluated.

The constructed response 104 is received at a computer-implemented assessment engine 102. Also received at the computer-implemented assessment engine 102 is an electronic process log 106 associated with the response 104. As referred to herein, an "electronic process log" comprises data indicative of writing processes utilized by the user in generating the constructed response 104. The electronic process log 106 may thus reflect the user's writing behavior, including planning, revising, and editing performed by the user in generating the constructed response 104, among other behavior. In an example, the electronic process log 106 comprises a plurality of time-stamped entries, with each of the entries (i) being associated with a keystroke, or other action, made by the user in generating the constructed response 104, and (ii) indicating a change in the text of the constructed response 104 due to the keystroke or action (e.g. mouse action, etc.). In this example, the electronic process log 106 is not merely a "keystroke log." Conventional keystroke logs only provide information on which key was pressed. By contrast, the electronic process log 106 utilized herein provides information on (i) which key was pressed or what action was taken, and (ii) how the text changed due to the keypress or action. In some embodiments, the electronic process logic 106 may further include data reflecting linguistic analyses of time-stamped actions.

The computer-implemented assessment engine 102 is configured to process the constructed response 104 and the electronic process log 106. In processing the constructed response 104, the assessment engine 102 is configured to generate first feature values representative of aspects of the constructed response 104. Such first feature values may correspond to features used in conventional automated scoring systems known to those of ordinary skill in the art. For instance, the first feature values may correspond to features utilized in the E-rater essay scoring system, which is the property of Educational Testing Service. The E-rater essay scoring system, described in U.S. Pat. Nos. 6,181,909 and 6,366,759 to Burstein et al., which are incorporated herein by reference in their entireties, utilizes features relating to (i) content of the constructed response, (ii) lexical complexity of the constructed response, (iii) grammar, usage, mechanics, and style errors of the constructed response, and (iv) organization of the constructed response, among others. It is noted that the first feature values generated by the computer-implemented assessment engine 102 may correspond to various other features utilized in automated scoring systems. The first feature values are representative of aspects of the final written product produced by the user (i.e., the submitted constructed response 104).

As noted above, the computer-implemented assessment engine 102 is further configured to process the electronic process log 106. In processing the electronic process log 106, the assessment engine 102 is configured to generate second feature values that are related to the user's actions in generating the constructed response 104. As described above, the process log 106 includes time-stamped data indicating behavior of the user (e.g., planning, editing, etc.) in generating the constructed response 104. Thus, the second feature values are indicative of the process utilized by the user in generating the constructed response 104, as opposed to the final written product produced by the user. The second feature values derived from the electronic process log 106 are described in further detail herein and may include (i) data indicating types of actions performed by the user (e.g., pauses, deletions, insertions, copying, pasting, jumping, strike out, formatting changes, organizational changes, etc.), (ii) time points associated with the actions (e.g., points in time in composition process at which the actions occurred), (iii) locations associated with the actions (e.g., indicating, for example, whether the actions occurred within a word, between words, within a phrase, between phrases, within a sentence, between sentences, within a paragraph, or between paragraph, etc.), and (iv) duration of the action in terms of the time elapsed or text length, or (v) any other relevant data.

Where the response is generated collaboratively by multiple users, the process log may contain data about which user entered which actions.

The second feature values derived from the electronic process log 106 may also include values based on inter-word intervals (IWIs). An IWI, as referred to herein, comprises an indication of an amount of time that the user paused between typing two adjacent words of the constructed response 104 (e.g., an amount of time that the user paused between typing a last letter of a first word and a first letter of a second word, with the second word being adjacent to the first word in the constructed response 104). Other second feature values utilized in embodiments are based on amounts of time that the user paused between typing (i) two adjacent characters (i.e., inter-key intervals), (ii) two adjacent phrases (i.e., inter-phrase intervals), and (iii) two adjacent sentences (i.e., inter-sentence intervals), among others.

Additional other second feature values may be used in the approaches described herein. Such other second features may indicate (i) a total time the user spent producing the constructed response, (ii) a typing speed of the user (e.g., a number of keystrokes divided by the total time), (iii) a time spent by the user on editing behaviors (e.g., time spent on cut/paste/jump events, normalized by total time), (iv) a rate of typo correction (e.g., log odds of correcting a spelling error versus leaving it uncorrected), and (v) an amount of discarded text (e.g., proportion of events in the electronic process log that involve deletions rather than insertions), among other metrics.

As referred to herein, a "feature" may be composed of a multiplicity of independent sub-features. For example, a second feature that may be used in the approaches described herein comprises a vector including information on a plurality of IWIs. The vector may include, for each of the M longest IWIs associated with the constructed response 104, (i) a duration of time of the IWI (e.g., an amount of time in seconds), and (ii) an associated time point, with the time point indicating a point in time at which the associated pause occurred. For example, for an IWI having a duration of 3.0 seconds, with the pause starting at a time x and ending at a time (x+3.0 seconds), the associated time point may be a median time point of the total time period of the duration, such that the associated time point for the IWI is a time (x+1.5 seconds). It is noted that in examples described herein, the associated time points of the vectors are normalized. For example, in embodiments, all associated time points have values between 0.0 and 1.0, regardless of a length of time that a user spent in typing the constructed response. M is a predetermined integer value, such as 25 (e.g., the vector includes information on the 25 longest IWIs for the constructed response, in an example). By limiting vectors to including information on only the M longest IWIs and by normalizing the associated time points, vectors associated with different constructed responses may be compared and scored accordingly. Computing the above-described vector feature may include determining from the electronic process log 106 various sub-features (e.g., intervals of time between the user's keystrokes in generating adjacent words of the constructed response 104) and processing the sub-features to determine the vector feature.

In other embodiments, second features utilized in the approaches described herein include information on the user's pauses in generating the constructed response. These second features may include (i) durations of time that the user paused between typing adjacent words, letters, phrases, and/or sentences of the constructed response, and (ii) information associated with the pauses, with such information indicating a point in time at which the associated pause occurred and/or whether the pause occurred within a word, between words, within a phrase, between phrases, within a sentence, between sentences, within a paragraph, or between paragraphs, among other information.

In examples, the computer-implemented assessment engine 102 automatically generates a score 108 without subjective human judgment by applying a computer scoring model (e.g., a statistical computer model) to the first feature values (i.e., those feature values representative of aspects of the constructed response 104) and/or to the second feature values (i.e., those feature values related to the user's writing behavior in generating the constructed response 104). The computer scoring model may be part of an automated scoring system for automatically scoring the constructed response 104 without human intervention (or requiring only minimal human intervention). The computer scoring model is described in further detail below with reference to FIG. 2A.

The computer-implemented assessment engine 102 also automatically generates information on the user's writing behavior 110 based on the second feature values and without subjective human judgment. The information 110 may include a second score (e.g., a score that is different from the score 108) relating to one or more aspects of the user's writing processes and/or a piece of feedback. For example, the piece of feedback could be a text string stating, "The student takes time to plan his or her sentences and paragraphs and then produces text efficiently in longer bursts. These are characteristics of a stronger writer." As another example, the piece of feedback could be a text string stating, "The student's writing process is rather fragmented and the resulting texts are disconnected." The information on the user's writing behavior 110 is generated automatically based on the second feature values and without human intervention (or requiring only minimal human intervention). In examples, the information 110 may also be based on the first feature values (i.e., feature values derived from the constructed response 104). The information 110 may be used to provide a richer understanding of student performance that is not reflected in the score 108. For example, the user may receive a score 108 that is relatively low for a variety of reasons. The information 110 may provide an indication of why the student received the low score (e.g., the user has poor keyboarding skills, the user does not edit his or her work, etc.). In such a case, a piece of feedback may be generated, without human intervention and accounting for both first features and second feature, that states "The student takes time to plan his or her sentences and paragraphs and then produces text efficiently in longer bursts. But the student makes careless mistakes when typing and does not edit accordingly."

Conventionally, automated scoring systems assess constructed responses based only on the final written products produced by users. Thus, the conventional systems provide no information about planning, revision, editing, and other processes performed by users in generating the final written products. By contrast, the systems and methods described herein use process logs to gain a richer understanding of student performance and do not consider only the students' final written products. The approaches described herein enable the use of process logs (i) to provide richer validation information about assessments; (ii) to detect patterns of student responses that may be indicative of undesirable behaviors (e.g., lack of motivation, plagiarism, etc.) that may affect the validity and interpretation of scores; (iii) to support more accurate automated scoring; (iv) to provide evidence on how different population groups (males vs. females; black vs. white; older vs. younger; native English speakers vs. non-native English speakers) may approach the writing task; and (v) to provide feedback to teachers, students, and other persons about writing performance, among other uses. It should thus be appreciated that the systems and methods described herein enable the providing of meaningful feedback that goes beyond a mere score for the final written product.

From an assessment perspective, evaluating writing processes can be valuable for at least two reasons. One is to give teachers and students feedback (e.g., diagnostic feedback) to improve writing practice. Such feedback may include scores and/or other information on a user's writing behavior. As a simple example, a limited time on task might suggest a lack of motivation, engagement, or persistence. Similarly, an absence of editing behavior, in combination with disjoint text (e.g., containing substantial amount of grammatical and mechanical errors interfering the flow and meaning of the text), might prompt attention to teaching editing and revision strategies. An additional potential value is to characterize differences among subpopulations beyond the quality of the final product, such as mechanical characteristics of text production (e.g., typing speed, extent of editing) and writing patterns and styles (e.g., lack of planning, level of fragmentation of the writing processes).

Figure 2A:
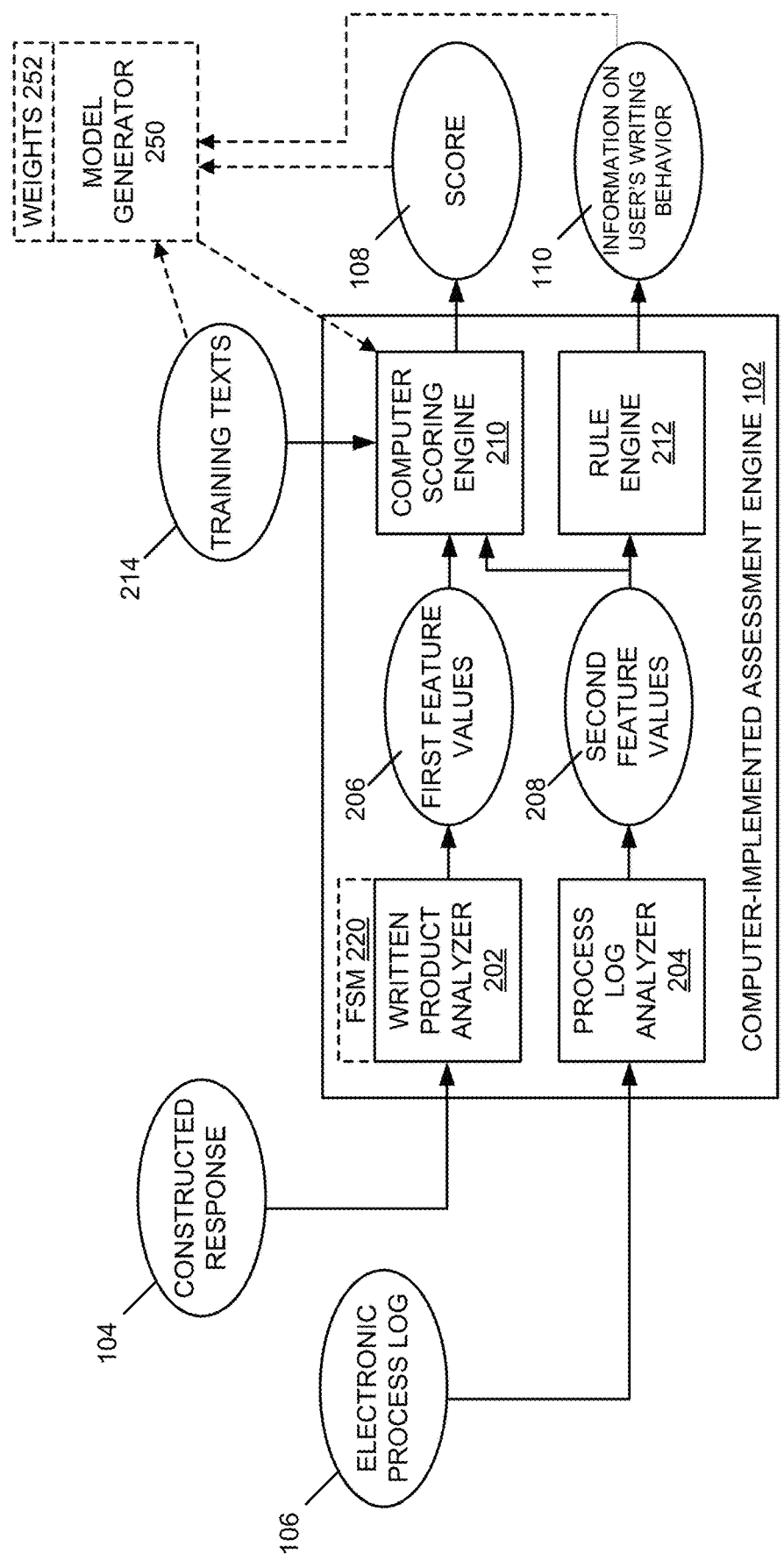
FIG. 2A is a block diagram illustrating a computer-implemented assessment engine in accordance with disclosed embodiments.

FIG. 2A is a block diagram including additional details on the computer-implemented assessment engine 102 of FIG. 1. As shown in FIG. 2A, the constructed response 104 is received at a written product analyzer 202. The written product analyzer 202 is configured to process the constructed response 104 to generate first feature values 206 representative of aspects of the constructed response 104. In an example, the first feature values 206 include numerical measures or Boolean values that are representative of aspects of the constructed response 104.

The written product analyzer 202 may perform various text processing on the constructed response 104. For instance, the written product analyzer 202 may employ a finite state machine (FSM) 220 to recognize linguistic boundaries (e.g., word, sentence, and paragraph) in the constructed response 104. The recognizing of these linguistic boundaries may also employ conventional, automated, computer-based algorithms known to those of ordinary skill in the art. Various other processing and analysis may be performed on the constructed response 104 at the written product analyzer 202, such as correction of spelling errors in the constructed response 104, using conventional, automated, computer-based algorithms known to those of ordinary skill in the art. The use of spelling correction algorithms can be beneficial to improve the quality of the assessment being carried out by reducing the likelihood of complications in the assessment caused by the presence of spelling errors.

The electronic process log 106 is received at a process log analyzer 204. The process log analyzer 204 is configured to process the electronic process 106 to generate second feature values 208 related to the user's actions (e.g., planning actions, editing actions, revising actions, etc.) in generating the constructed response 104. In an example, the second feature values 208 include numerical measures or Boolean values. The process log analyzer 204 may perform various processing of the electronic process log 106 and the feature values derived therefrom in generating the second feature values 208. In examples, the second feature values 208 comprise a vector. The vector may include (i) data indicating types of actions performed by the user (e.g., pauses, deletions, insertions, copying, pasting, jumping, etc.), (ii) time points associated with the actions (e.g., points in time in composition process at which the actions occurred), (iii) locations associated with the actions (e.g., indicating, for example, whether the actions occurred within a word, between words, within a phrase, between phrases, within a sentence, between sentences, within a paragraph, or between paragraph, etc.); and (iv) duration of the action in terms of the time elapse or text length. For example, when the action is a "pause," the vector may further include durations of time indicating how long the user paused between typing adjacent words, letters, phrases, sentences, or paragraphs of the constructed response.

In the example of FIG. 2A, the first feature values 206 and/or the second feature values 208 are received at a computer scoring engine 210. The computer scoring engine 210 includes an automated scoring system configured to determine the score 108 for the constructed response 104 without subjective human judgment. The score 108 may measure various aspects of the constructed response 104 (e.g., a content of the response 104, a lexical complexity of the response 104, grammar, usage, mechanics, and style of the response 104, vocabulary utilized in the response 104, English language proficiency utilized in the response 104, etc.). The score 108 may be a point score (e.g., 87 points out of 110 points possible), a percentage or decimal score (e.g., 95% correct), a classification (e.g., "high," "medium," "low," etc.), or a ranking, for example.

In an example, the computer scoring engine 210 is a computer-based system for automatically scoring the constructed response 104 that requires no human intervention or minimal human intervention. The scoring engine 210 may determine the score 108 for the constructed response 104 based on the first and second feature values 206, 208 and a scoring model (e.g., a statistical computer scoring model). In examples, the scoring model includes weighting factors for the feature values 206, 208, and the weighting factors are determined based on a plurality of human-scored constructed responses 214. Such human-scored constructed responses 214 may be referred to herein as "training texts." The scoring model may utilize a scoring equation. It is noted that in some examples, weighting factors of the scoring model are judgmentally determined and in a manner which is not necessarily statistical.

The scoring model may be a numerical model that is applied to the first and second feature values 206, 208 to determine the score 108. In an example, the scoring model comprises variables and associated weighting factors, with each of the variables receiving a feature value of the first and second feature values 206, 208. By applying the scoring model to the first and second feature values 206, 208 in this manner, the score 108 is determined.

To generate the scoring model used in the computer scoring engine 210, the engine 210 may receive the plurality of human-scored constructed responses 214 with associated scores for each of the constructed responses 214. The engine 210 or a model generation module included therein uses the plurality of human-scored constructed responses 214 to determine the weighting factors for the model, e.g., through a regression analysis (e.g., a "leave-one-out" multiple linear regression analysis, etc.). The plurality of human-scored constructed responses 214 may span a range of reference scores, and the constructed responses 214 may be previously scored constructed responses that have been accepted as usable for training the scoring model. In an example, the weighting factors of the model may be determined via a machine learning application trained based on the plurality of human-scored constructed responses 214. Specifically, the machine learning application may utilize a linear regression analysis, a logistic regression analysis, or another type of algorithm or analysis (e.g., a random forest learning analysis, decision tree analysis, random tree analysis, Classification And Regression Tree (CART) analysis, etc.).

With the scoring model in place, the score 108 may be determined by applying the scoring model to the first and second feature values 206, 208, as noted above. It should be appreciated that under the approaches described herein, one or more computer-based models are used in determining the score 108. As described above, such computer-based models may be trained via a machine-learning application in order to determine weighting factors for the models. By contrast, conventional human scoring techniques for determining a score for a constructed response include none of these steps. Conventional human scoring techniques involve one or more human graders reviewing constructed responses and manually assigning scores to the constructed responses.

The second feature values 208, in addition to being received at the computer scoring engine 210 in the example of FIG. 2A, are received at a rule engine 212. In an example, the rule engine 212 includes multiple rules that each include (i) a condition, and (ii) an associated action. The rule engine 212 applies the conditions to the second feature values 208 and determines one or more rules of the multiple rules that are satisfied. A rule of the rule engine 212 is satisfied when one or more feature values of the second feature values 208 meet a condition associated with the rule. The rule engine 212 performs an action associated with the satisfied rule to generate the information on the user's writing behavior 110. As noted above, the information 110 may include (i) a score relating to one or more aspects of the user's writing processes or behaviors, and/or (ii) a piece of feedback. Thus, the performing of the action associated with the satisfied rule may include calculating a score (e.g., a second score that is different from the score 108) based on the one or more feature values that meet the satisfied rule's condition or returning feedback including a predetermined response, among other actions. The calculation of the scores and feedback are performed by the rule engine 212 without subjective human judgment. In an example, the predetermined response includes a fixed text string or a template with variables that are filled based on the one or more feature values that meet the satisfied rule's condition.

The example of FIG. 2A depicts the rule engine 212 receiving only the second feature values 208 from the process log analyzer 204. In other examples, the rule engine 212 also receives the first feature values 206 from the written product analyzer 202. In these other examples, the rule engine 212 applies the conditions of its rules to both the first and second feature values 206, 208 to determine one or more rules that are satisfied. An action or actions are performed based on the one or more satisfied rules to generate the information on the user's writing behavior 110. Thus, under the approaches described herein, the information 110 is generated by applying the computer-based rule engine 212 to the second feature values 208 or to both of the first and second feature values 206, 208. The rule engine 212 includes multiple (e.g., tens, hundreds, thousands, etc.) rules, with each of the rules including a condition and an associated action. By contrast, conventional human techniques for providing information on a user's writing behavior do not utilize such computer-based rule engines. The conventional human techniques include one or more humans monitoring students as they perform a test and manually providing feedback on the student's writing behavior, requiring live observation of test-taking. Comprehensive evaluation of all students would require 1:1 student-teacher ratios. Also, the conventional human techniques would not include use of the above-described electronic process logs. The use of the electronic process logs permits every student interaction with a keyboard (e.g., every keystroke and the effect of that keystroke on the constructed response) to be recorded with a precise timestamp and analyzed. A human who manually monitors students could not detect and make note of every such student interaction with a keyboard, nor could the human precisely record timestamps of each interaction. Additional distinctions between the approaches described herein and conventional human techniques are described throughout this disclosure. The approaches described herein are rooted in computer technology and are vastly different than conventional human techniques, as noted above. Accordingly, it is evident that the approaches described herein are not mere computer implementation of conventional human techniques and indeed are vastly different from such.

Figure 2B:
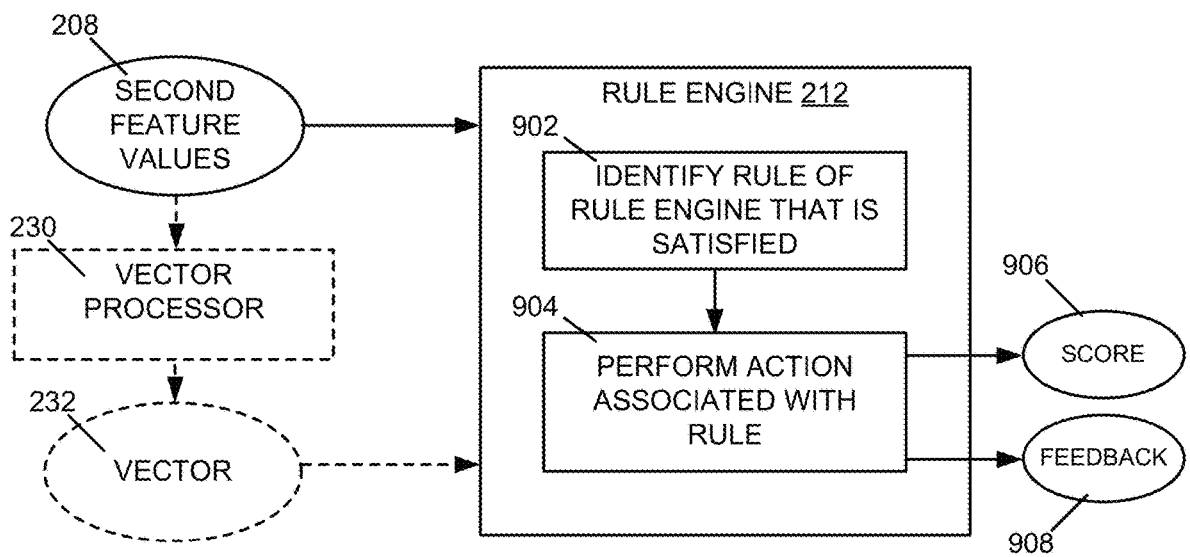
FIG. 2B is a block diagram illustrating a computer-implemented rule engine in accordance with disclosed embodiments.

FIG. 2B depicts the rule engine 212 of FIG. 2A and example steps that may be performed by the rule engine 212. As described above, second feature values 208 derived from an electronic process log are received at the rule engine 212. In embodiments, unfiltered or raw second feature values 208 may be processed before being received at the rule engine 212. In some cases, that processing may include generating a vector 232 relying on a vector processor 230, or engine, that receives all the generated second feature values 208 and generates a vector 232 based on one or more data filters, conditions, parameters, or rules (e.g. a vector generated based on six-hundred received second feature values indicative of all of a user's actions during response construction responsive to an evaluation item may be filtered according to various rules and conditions to obtain the longest 25 inter-word intervals (IWIs), i.e., pauses between typing two adjacent words of the constructed response). In some aspects the vector processor 230 may also include first feature values, or other relevant information in the vector 232. This vector 232 may then be passed to the rules engine 212. In some examples, the rule engine 212 also receives first feature values 206 derived from the constructed response (i.e., the final written product). The rule engine 212 takes the constellation of received feature values (i.e., second feature values or a combination of first and second feature values or a vector) and applies a series of condition/action pairs specified in a rulebase. Rules in the rulebase are triggered when feature values for a response match a condition defined in the rulebase. Thus, at 902, a rule of the rulebase that is satisfied is determined. At 904, one or more actions associated with the satisfied rule are performed. The actions may include calculating a score 906 as a combination of feature values or returning feedback 908 in the form of a pre-stored response. Pre-stored responses can be fixed strings or they can be templates which include variables conditionally filled depending on the value of a feature or an expression derived from a set of features.

The feedback 908 provided by the rule engine 212 may relate to behavioral patterns of users' writing processes. For example, more capable writers (e.g., as evidenced by higher human scores on text production quality) may spend more time on producing more texts in longer bursts, revise and replace previous texts with different content (e.g., in contrast to the same content), and show more deliberation about word choice. Thus, the feedback 908 may highlight such actions performed by the user and note that they are actions performed by more capable writers. Less capable writers may show more hesitancy (or disfluency) during writing. Less capable writers may pause longer before starting to write, pause longer at beginnings of the words and at white space, pause longer inside words, and produce letters at a relatively low rate. The feedback 908 may highlight such actions performed by the user and note that they are actions performed by less capable writers. The feedback 908 may relate to categories of behavioral patterns such as (a) latency and typing fluency, (b) phrasal and chunk level text deletion and editing, (c) word-level editing involving monitoring the typing as text being produced (e.g., not just proofreading), and (d) planning and deliberation at the sentence level, and above.

As described above, second feature values derived from the electronic process log 106 may be used to generate a vector that includes information on user actions. Such actions include, for example, insertion actions, deletion actions, jumping actions, copying actions, and pasting actions, among others. Thus, in examples, the vector includes (i) data indicating types of actions performed by the user (e.g., pauses, deletions, insertions, copying, pasting, jumping, etc.), (ii) time points associated with the actions (e.g., points in time in composition process at which the actions occurred), (iii) locations associated with the actions (e.g., indicating, for example, whether the actions occurred within a word, between words, within a phrase, between phrases, within a sentence, between sentences, within a paragraph, or between paragraph, etc.), and (iv) duration of the action in terms of the time elapse or text length. When the action is a "pause," for instance, the vector may further include durations of time indicating how long the user paused between typing adjacent words, letters, phrases, sentences, or paragraphs of the constructed response. The vector is limited to a predetermined size (e.g., a predetermined number of elements), thus allowing vectors associated with different constructed responses to be compared. Feedback may be generated based on the comparisons.

To illustrate the use of vectors in this manner, an example is described below. In this example, the vector specifically includes information on IWIs. It should be appreciated that pauses are merely one type of user action that may be included in a vector, e.g. 232. In other examples, a vector 232 includes information on other types of user actions (e.g., deletions, insertions, copying, pasting, jumping, etc.), as described above. It is thus noted that the approaches described herein are not limited to the specific example described below (e.g., not limited to a vector based solely on IWIs). It is further noted that other types of pauses (e.g., inter-key intervals, inter-phrase intervals, inter-paragraph intervals, etc.) and actions (e.g., pasting, jumping, highlighting, etc.) may be analyzed using the approaches described herein.

In the example embodiment that analyzes IWIs, IWIs may be analyzed (1) to distinguish writing patterns and styles, and (2) to provide scores and/or feedback. To illustrate IWI features that may be derived from an electronic process log, reference is made to FIG. 3. This figure provides a dendrogram visualization of the IWI duration using one essay as an example. The original essay reads as follows: "I think the community should build a swimming pool because i believe you can I maintain a healthier lifestyle and have fun while doing it has more potential to benefit more people than a foreign exchange. The whole community can benefit the pool but only a select few would benefit from the exchange program." In FIG. 3, the words of the essay are listed along the x-axis of the dendrogram. The height of the horizontal lines that connect two words (i.e., the ones with the shortest distance on the time dimension from two clusters) represents the IWI duration in seconds, as shown on the y-axis.

Figure 3:
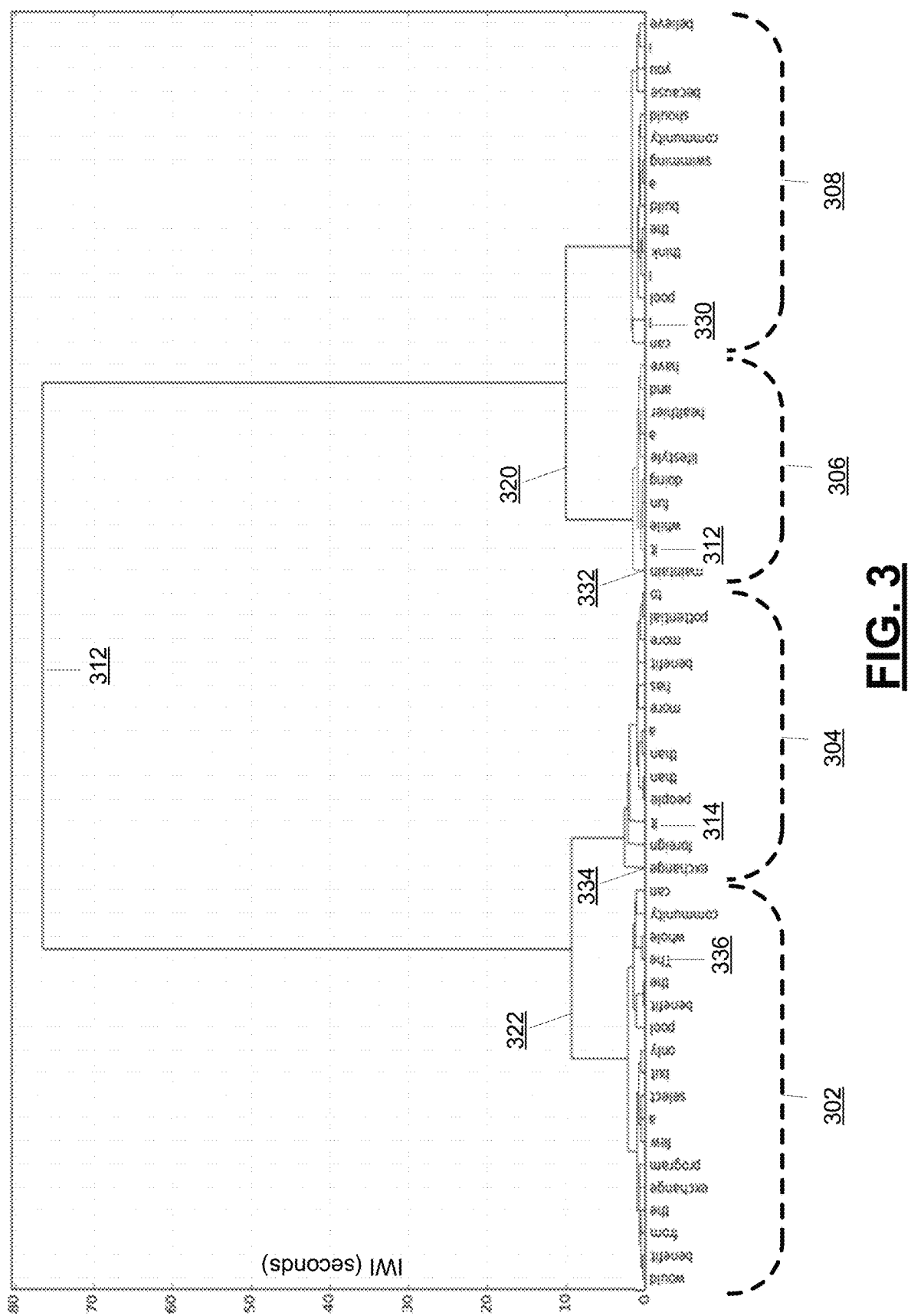
FIG. 3 illustrates a clustering analysis based on process log data in accordance with disclosed embodiments.

In the example of FIG. 3, the three longest between-word pauses all happen at the phrasal and sentence boundaries, which naturally separate the text production into four bursts. Specifically, the pause 310 between "it" 312 and "It" 314 is the longest with more than 70 seconds, with "it" on the end of the first sentence and "It" being the first word of the following sentence (note the user omitted a period (.) between these sentences in the essay). It is reasonable to assume that the student spent a fair amount of time planning the second sentence or reading and evaluating the source materials. The pauses 320, 322 between the words "I" 330 and "maintain" 332 (where "I" is likely to be a typo), and the words "exchange" 334 and "The," 336 both occur at reasonable junctures between long chunks, each pause lasting for about 10 seconds. A sensible explanation for these relatively long pauses is that the student was deliberating on the choice of words and sentence structure. All the other IWIs in this example were less than 2 or 3 seconds. Thus each burst-cluster of the essay 302, 304, 306, 308, with pauses inserted, is as follows:

CLUSTER 4 308: "I think the community should build a swimming pool because i believe you can I [approximately 10 second pause 320]"

CLUSTER 3 306: "maintain a healthier lifestyle and have fun while doing it [approximately 70 second pause 312]"

CLUSTER 2 304: "It has more potential to benefit more people than than a foreign exchange. [approximately 10 second pause 322]"

CLUSTER 1 302: The whole community can benefit the pool but only a select few would benefit from the exchange program."

The IWIs can provide temporal evidence about the essay composition process, and it may be desirable to quantify and summarize this information in a way that can be used to make meaningful distinctions among groups of students. A practical challenge is how to align the IWIs from different electronic process logs so that writing patterns can be compared despite differences in (i) the amounts of time that individual students spend on writing, and (ii) the number of words each of the students produces. To address this challenge, in the approaches of the instant application, information about longer pauses (e.g., pauses likely to reflect strategic planning and processing) is considered. These pauses are further considered in terms of their temporal position in the student's writing process. The approaches of the instant disclosure consider, specifically, the longest IWIs of an essay (e.g., the 25 longest IWIs of an essay). First, for each electronic process log, the IWIs are ranked from longest duration to shortest duration. Then, the duration of the IWI (i.e., the amount of time of the IWI) and its normalized median time point along the time axis are selected as two indicative variables to represent each electronic process log. Median time points are discussed above. For example, as noted above, each IWI has an associated time point, with the time point indicating a point in time at which the associated pause occurred, and in embodiments, the associated time point is a median time point of the total time period of the duration. By placing these indicative variables one after another based on the rank ordering of the IWI duration, a vector of IWI for each electronic process log is formed. Subsequently, for all vectors (from different electronic process logs associated with different essays) to have the same length, each vector is truncated by introducing a cut-off in the rank ordering. In one example, the 25 longest IWIs are chosen as the cut-off rank.

Through this aligning procedure, each electronic process log, in the example above, is represented by an IWI vector with 50 elements that capture the duration and temporal location (e.g., median time-points) of the 25 longest IWIs. The similarity or difference among logs can then be determined using the IWI vectors. To align electronic process logs of different lengths of time, the median time-points of the IWIs are normalized by the total writing time, such that each median time point is within the range between zero and one. In various embodiments, the normalizing range can be any range (e.g. between zero and 100).

To illustrate the information that may be included in a vector for an essay, reference is made to FIGS. 4A and 4B. In FIG. 4A, 25 bars are shown, with each of the bars representing one of the 25 longest IWIs of an essay written by a first student. Likewise, in FIG. 4B, 25 bars are shown, with each of the bars representing one of the 25 longest IWIs of an essay written by a second student. The vertical axis indicates the length of IWIs in seconds, and the horizontal axis gives the corresponding median time-point of an IWI. The median time-point in this example computed as the mid-point of the absolute time between two adjacent words. For example, if the last character of the first word is typed at a time "minute 1 second 30," and the first character in the following word is typed at a time "minute 1 second 40," the median time-point of the IWI is at a time "minute 1 second 35." Also provided in the graphs are the total number of words in the final product and a score assigned to the essay by a human.

As can be seen, the two individual electronic process log examples of FIGS. 4A and 4B, respectively, are drastically different. FIG. 4A shows that the first student has made few relatively long inter-word pauses, with four instances standing out as particularly extensive (i.e., greater than 20 seconds). FIG. 4B shows a very different pattern of IWI duration and median time-point. Compared to the example above, the longest 25 IWIs in FIG. 4B are somewhat more evenly distributed throughout the composition and the length of the durations appears to vary less across the 25 IWIs. By normalizing the median time-point by the total writing time, the confounding factor of time on task (which also relates to the essay length) is eliminated. FIGS. 4A and 4B suggest that the IWI information provides a different type of evidence about writing proficiency than the essay length and human scores on essay quality. The decision to restrict attention to the longest 25 IWIs is motivated by the overall distribution of IWIs, which follows a heavily skewed distribution in which almost all IWIs are very short (less than half of a second). The desired number of IWIs to include in a particular vector for a particular evaluation will vary from case to case.

Although the example above describes the use of a vector with 50 elements (e.g., durations of the 25 longest IWIs, and median time points associated with each of the 25 IWIs), in other examples, vectors including additional information are utilized. In an embodiment, variance values are calculated for IWIs that are between the 25 longest IWIs, and these variance values are included in the vectors. For example, FIG. 4A depicts bars 402 and 404 that represent two of the 25 longest IWIs of the essay. Between the time points associated with the bars 402 and 404, other IWIs occurred, but these other IWIs are not included in the group of the 25 longest IWIs, and so these other IWIs are not represented as bars on the graph. In examples, variances associated with the durations of the IWIs between the bars 402 and 404 are included in the vector associated with the essay, for example the between-cluster variances may be included in the vector. Likewise, within-cluster variances of IWIs between other bars of the graph are included in the vector associated with the essay, in embodiments. In some embodiments, (i) a variance of the durations of the IWIs between each set of adjacent bars is calculated, and (ii) these variances are summed. For example, the sum of the within-cluster variances or the between-cluster variances may be stored in the vector associated with the essay or stored and analyzed in another manner. In some embodiments, (i) for each gap between adjacent bars, a mid-point time-point is identified, and a duration of an IWI at the mid-point time-point is determined, and (ii) a variance of the durations of the mid-point IWIs is calculated. This variance may be stored in the vector associated with the essay or stored and analyzed in another manner. In addition to variances, a vector may include any relevant information for providing a score or feedback in an assessment. For example, additional information may include, e.g., pause duration, median time-point, whether the pause occurred within a word, between words, within a phrase, between phrases, within a sentence, between sentences, within a paragraph, or between paragraphs, a user's reference to external material such as a reference material or web content or hyperlinks or time spent reading a prompt or other written material, collaborative actions such as group messages written, etc.

Information (e.g., pause duration, median time-point, whether the pause occurred within a word, between words, within a phrase, between phrases, within a sentence, between sentences, within a paragraph, or between paragraphs, etc.) for the longest IWIs (e.g., 25 longest IWIs, etc.) of a constructed response may be analyzed in various ways. In some embodiments, constructed responses may be clustered into groups based on similarity measures (e.g., cosine similarity measures, Euclidean similarity measures, a Mahalanobis similarity measures, etc.) calculated between vectors storing IWI pause information. Such clustering is explained in further detail below with reference to FIGS. 5A-10. In other embodiments, the computer-implemented assessment engine 102 (e.g., as illustrated in FIGS. 1 and 2A and described above) derives the information on the longest IWI pauses (or any other relevant information) of a constructed response based on a received electronic process log 106. The computer-implemented assessment engine 102 uses the information as feature values that are received at a computer scoring engine 210 and/or rule engine 212. Using these feature values, a score 108 for the constructed response and/or feedback 110 on the user's writing process may be determined by the computer-implemented assessment engine 102. This approach is explained above with reference to FIGS. 1 and 2A and in further detail below. To illustrate applications of the aforementioned clustering and automatic scoring approaches embodiments are described below that take advantage of these approaches.

Clustering Approach to Analyzing Pause Features

In embodiments, IWI pause features (i.e., pauses between words) are analyzed using a clustering approach. It is noted, however, that in other embodiments, other features are analyzed using the clustering approach. These other feature can include different pause features such as pauses between letters (i.e., inter-key intervals), pauses between phrases (i.e., inter-phrase intervals), and pauses between sentences (i.e., inter-sentence intervals), among others. It is further noted that although the 25 longest IWIs are considered in the example below, in other examples, a different number of pauses are analyzed. For example, in other examples, the 50 longest IWIs or 100 longest IWIs (among other numbers of IWIs) are analyzed. Additionally, it is noted that information on other user actions (i.e., user actions other than pauses) may be analyzed using the clustering approach. In general, a vector including (i) data on types of actions performed by the user, (ii) time points associated with the actions, (iii) locations associated with the actions, and (iv) duration of the action may be generated and analyzed according to the clustering approaches described herein.

For example, two writing assessments are studied. One assessment from each of two writing purposes is used: Policy Recommendation and Argumentation. The targeted level is grade 7 for policy recommendation and grade 8 for argumentation. For each assessment, only an essay task is considered. Specifically, the policy recommendation essay tasks asks students to evaluate two proposals (i.e., on how to spend a generous monetary donation to the school) and write an essay recommending one policy over the other. The argumentation essay tasks asks students to take a position using reasons and evidence as to whether students should be rewarded for getting good grades. Students are provided with a planning tool and can access three source materials at any time.

Electronic process logging (e.g., which includes keystroke logging) is employed for data collection from which the duration and median time-point of the longest 25 IWIs were extracted. Several summary process features are obtained, including the total number of word inserts and total effective writing time for supplementary analyses.

A hierarchical cluster analyses is conducted based on similarity measures calculated between each IWI vector. Various similarity measures may be used. Such similarity measures include a cosine distance similarity measure, a Euclidean similarity measure, or a Mahalanobis similarity measure, among others. In the example described below, the hierarchical cluster analyses were conducted based on the cosine distances between IWI vectors using complete linkage. The cosine distance measure is used to decide whether the clusters are adequately different from one another.

After the number of clusters was determined, the clusters were examined and compared on several aspects. One aspect was the IWI duration and median time-point pattern. For this analysis, the time axis was divided into 10 bins, with each bin accounting for one tenth of the normalized total writing time. In the example described herein, 10 bins were used, but it is noted that a different number of bins is used in other examples. On one hand, the bin size needs to be large enough so that there are enough keystrokes in each bin. On the other hand, it needs to be small enough to show variations across bins. Second, the mean of the logarithm-transformed IWI duration values was computed in each bin separately for each cluster. This statistical transformation was undertaken in order to make the distribution of the IWI duration more similar to a normal distribution. Third, separately for each of the 20 bins (i.e., 10 bins in essay prompt), a two-sample independent t-test was conducted between the clusters on the mean log IWI values.

A second aspect used to compare clusters was the density distribution of the IWI duration and median time-point. Heat maps of the IWI duration were generated by median time-point to visually compare the probability of IWIs of certain lengths occurring at certain times in the writing process between clusters. To generate the density graphs, the x axis (normalized median time-point ranging from 0 to 1) was evenly divided into 100 steps, and the y axis (IWI duration ranging from 0 to 16 seconds) was evenly into 400 steps, which resulted in 100×400 blocks. In other examples, the x- and y-axes may be divided into different numbers of steps. The density of each block was calculated, and a normalized density distribution was produced in the form of a heat map for each cluster.

Finally, the clusters were compared based on the human ratings on text production skills, total number of words produced, and total writing time. The effect sizes were computed, and two-sample independent t-tests were conducted on the means of those measures between the clusters. Of note is that the total number of words produced is different from the traditional essay length. That is, words that were produced but deleted during the processes (and not appearing in the final product) were counted for this measure. Further, for total writing time, active writing time was used, which excluded pre-writing (i.e., pause before typing the first character), in order to be consistent with the timing data used for IWI analyses. Finally, due to the highly skewed distribution in human response time, logarithm-transformed values were used for these analyses.

Based on the criteria, two clusters were identified for both essay tasks, clusters 502, 504 for the first essay task and 506, 508 for the second essay task, as can be seen in FIGS. 5A and 5B. The cosine distance 620 between the two clusters is 0.63 for the policy recommendation essay as shown in chart 500a, and the cosine distance 522 between the two clusters is 0.62 for the argumentation essay as shown in chart 500b. This result indicates that the two clusters are weakly correlated (i.e., strongly separated). For both essays tasks, there are more essays in cluster 1 than in cluster 2.

Figure 6:
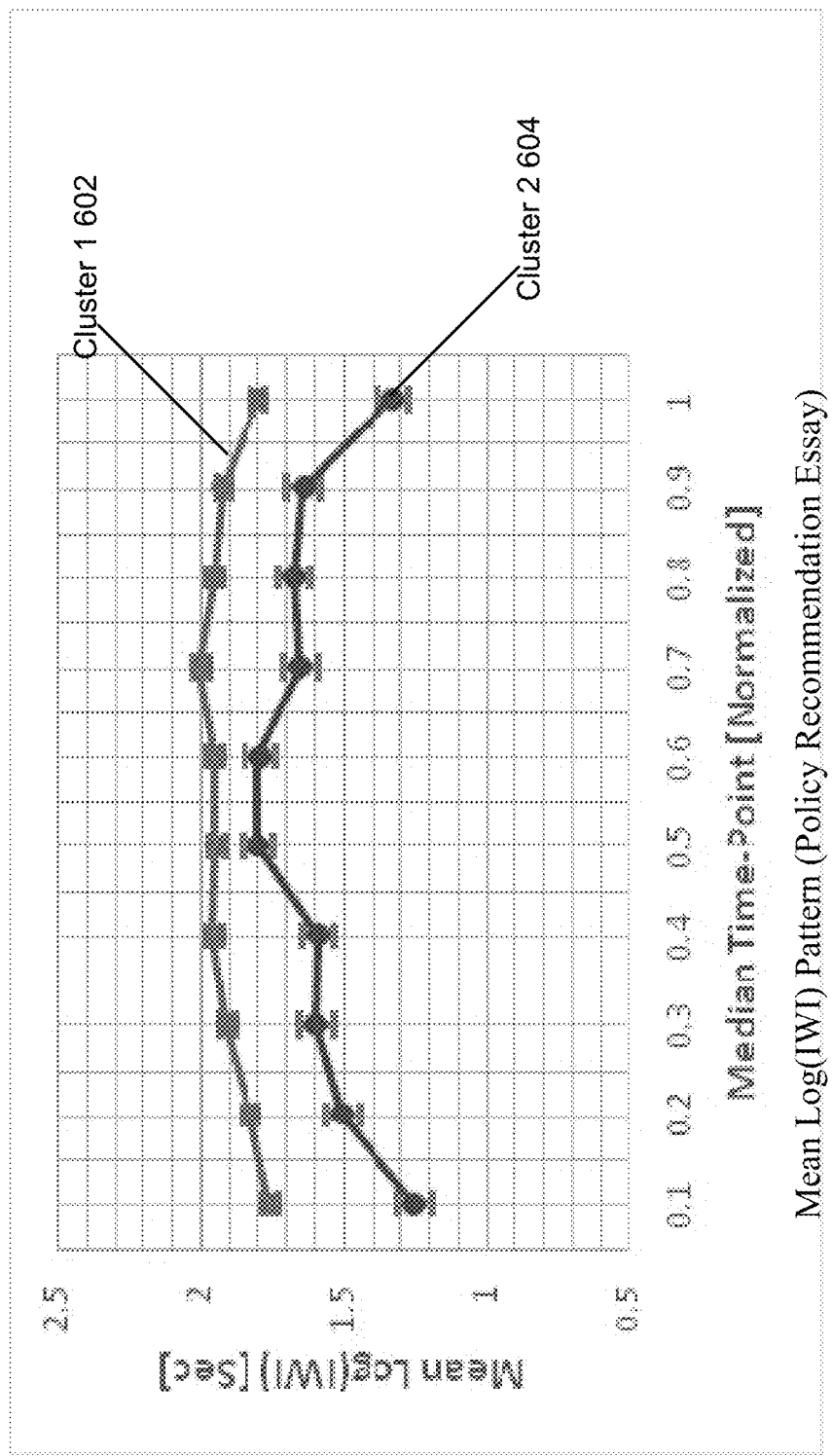
FIG. 6 illustrates an exemplary analysis based on process log data in accordance with disclosed embodiments.
Figure 7:
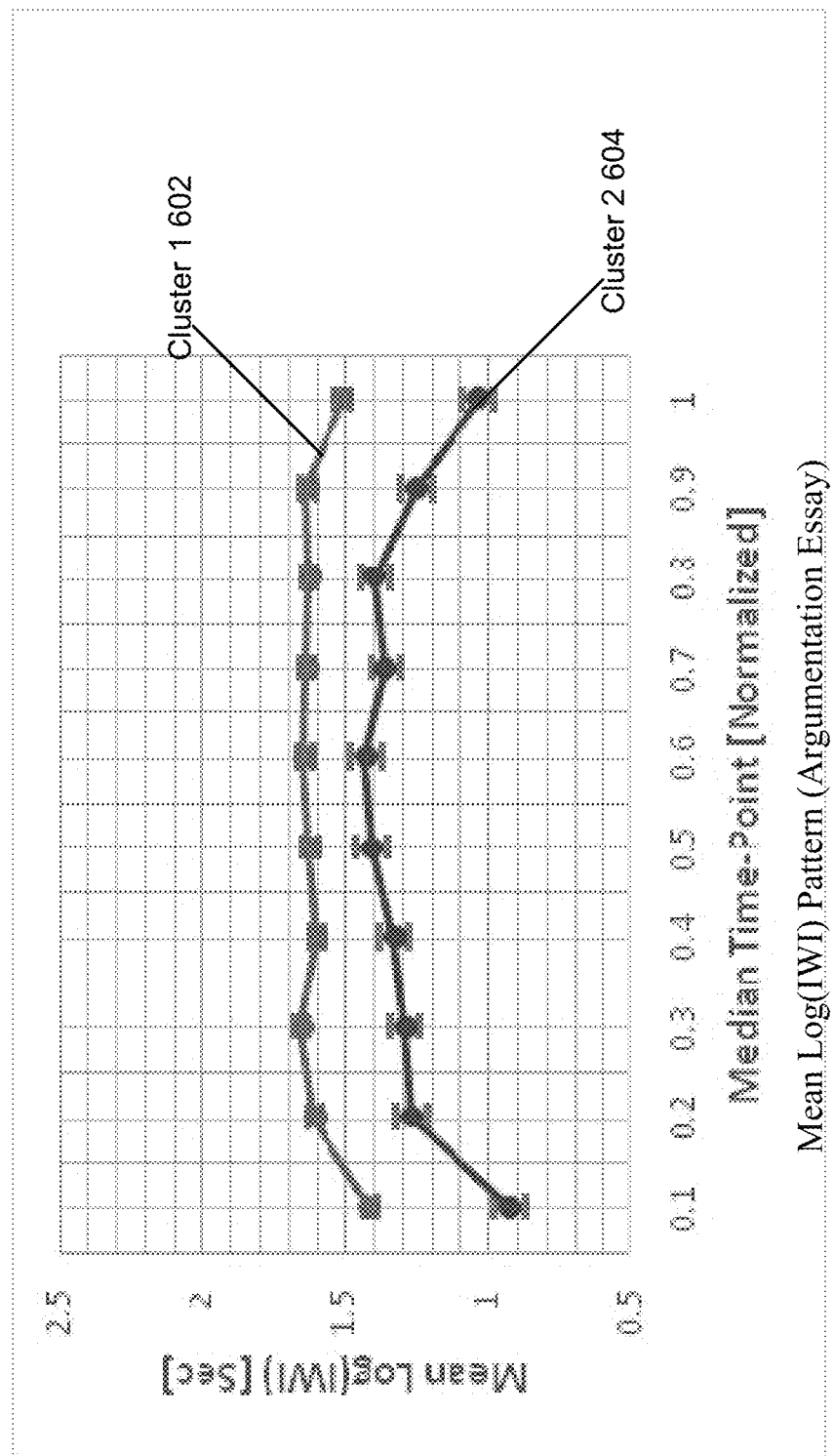
FIG. 7 illustrates an exemplary analysis based on process log data in accordance with disclosed embodiments.
Figures 9A, 9B:
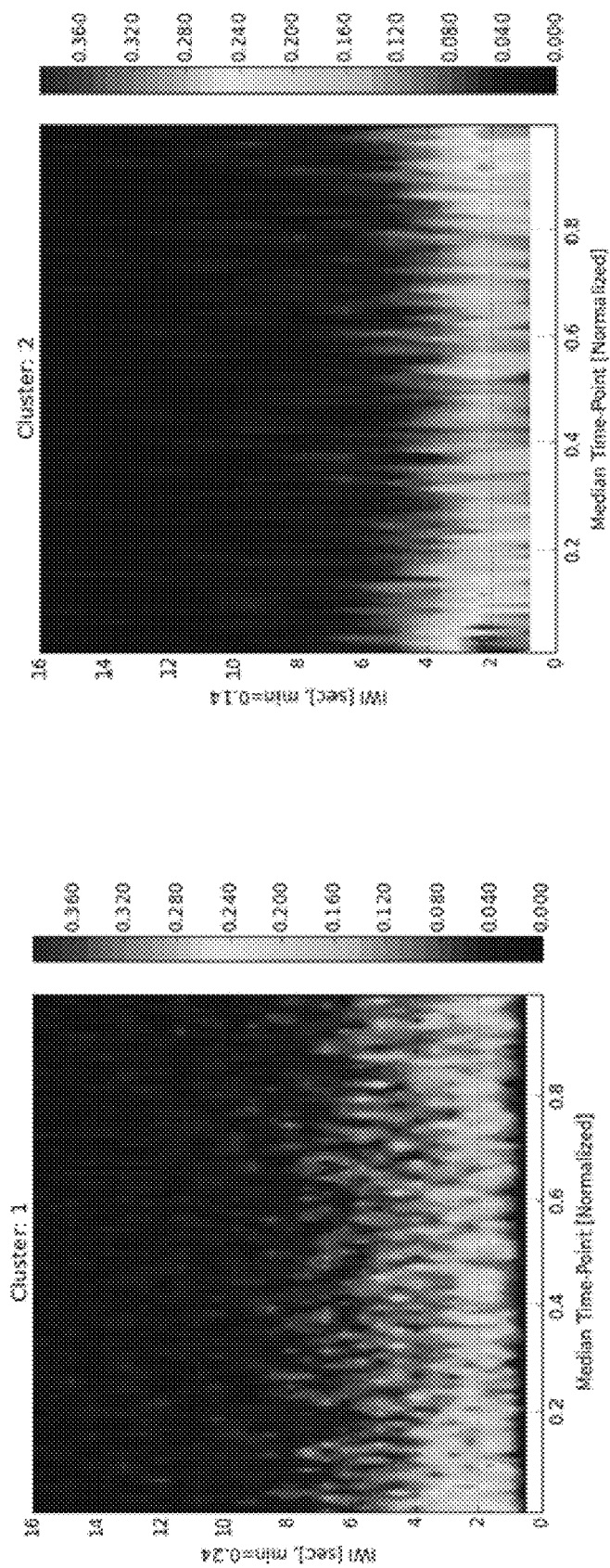
FIG. 9A illustrates an exemplary clustering analysis based on process log data in accordance with disclosed embodiments.
FIG. 9B illustrates an exemplary clustering analysis based on process log data in accordance with disclosed embodiments.

Next, the qualitative differences between the two clusters 602, 604 were examined. FIGS. 6 and 7 show the mean logarithm-transformed IWI duration at different median time-points in the writing process. Based on the t-test results, all pairs of comparisons suggested statistically significant differences (at a $p<0.05$) between the two clusters. Specifically, for both writing tasks, IWIs in cluster 1 602 were significantly longer than the ones in cluster 2 604 consistently throughout the composition. The differences appear to be smaller around the middle than at the two ends of the writing process. Additionally, it is worth noting that, for both essays, cluster 1 shows a more even straight-line pattern across median time-points than cluster 2, which appears to have a discernible drop in the IWI duration at the beginning and end of the composition process.

To further visually examine how the distribution of the IWIs from the two clusters differ, the density of IWI and the corresponding median time-points were plotted, as shown in FIGS. 8A, 8B, 9A, and 9B. The generation of the density graphs is described above. For cluster 1 on the policy recommendation essay, the density of IWIs appears to hover around 3-to-4 seconds throughout the text production process, with density shorter than two seconds fairly low. In contrast, the density pattern in cluster 2 is notably different, where there is a higher density with shorter IWIs at the beginning and the end of the composition process.

The contrast in IWI density pattern between clusters 1 and 2 is even more dramatic for the argumentation essay. Cluster 1 shows more evenly distributed IWIs hovering around 2 seconds throughout the composition, whereas cluster 2 exhibits more frequent and shorter pauses at the two ends of the writing process. These results of the contrasting IWI patterns between the two clusters also agree with the previous analyses presented in FIGS. 6 and 7.

FIG. 10 shows additional differences between the clusters. For both essays, cluster 1 writers were more able than cluster 2 writers, as evidenced by the higher human scores on the essay quality. Based on the t-test results, the average human scores for cluster 1 were both statistically significantly higher than cluster 2, and practically significant in terms of effect size. Cluster 1 also shows similarities to results in which students who scored higher spent more time on task, wrote longer essays, and were more fluent in executing critical writing processes.

In FIG. 10, "word insert" represents a sum of words that an author inserts which may or may not appear in the final product, and "writing time" represents the active composition time excluding pause time before the first keystroke. The rows "effect size" and "t-value" for the writing-time measure are based on log-transformed values.

Figure 10B:
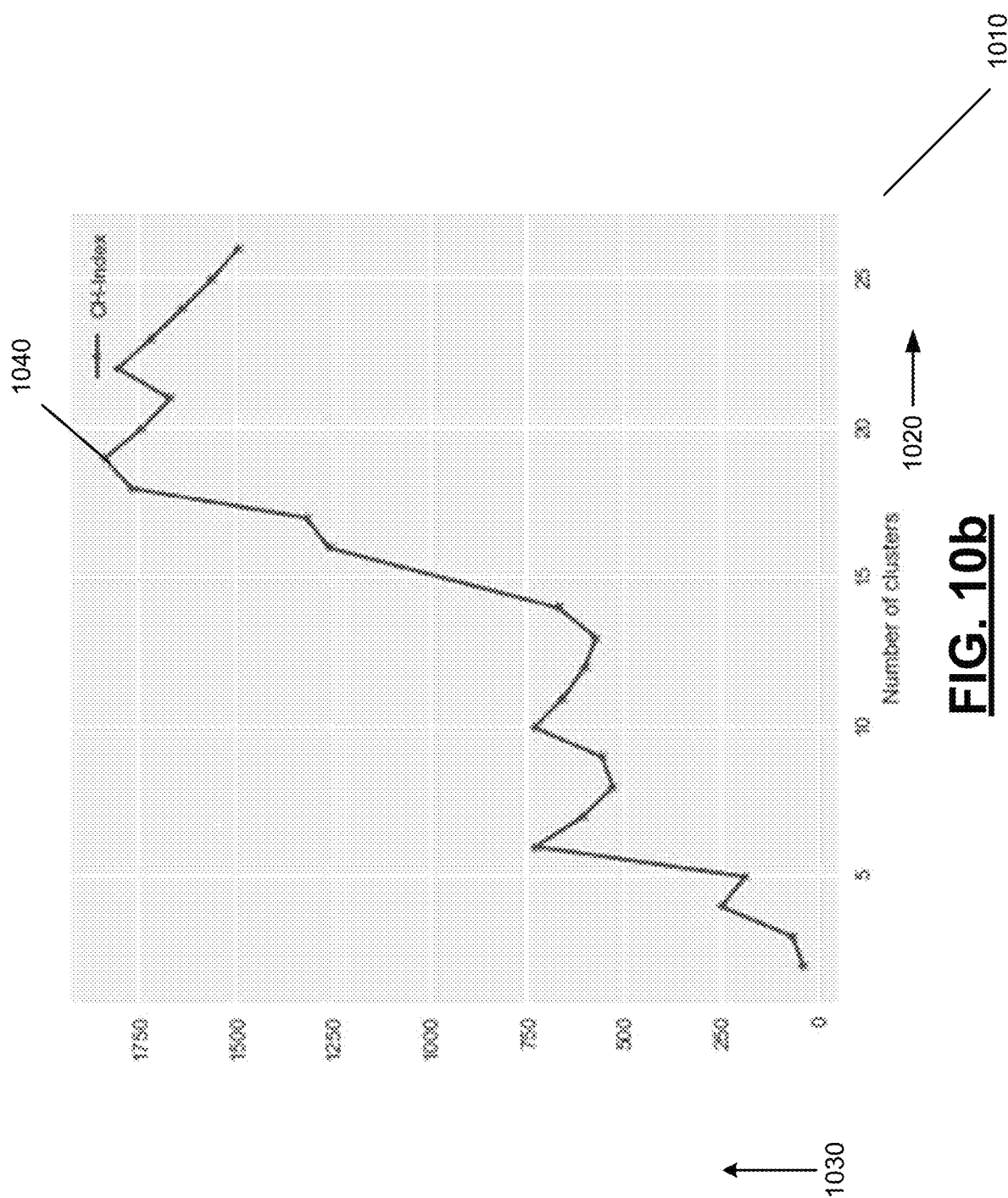
FIG. 10b illustrates an exemplary clustering analysis based vector data based in accordance with disclosed embodiments.

For a given feature analysis relying on vectors of a determined size, determining an appropriate or optimal cluster size may require its own analysis. For a given vector, or set of vectors, undergoing analysis, the optimal number of clusters chosen affects the information that may be gleaned. For example, a vector of 25 IWIs, divided into 25 clusters will result in 25 trivial clusters and remove most meaningful information that may be obtained from each cluster. Similarly, another trivial cluster is a single cluster of all 25 vector elements. Thus, in embodiments various techniques can be applied to help determine the number of optimal clusters. FIG. 10b depicts a chart 1010 illustrating application of a cluster optimizer function to identify the optimal number of clusters 1040 for vector analysis. A Calinski-Harabaz index 1030 is used, which relies on the within and the between cluster variances stored in a vector. Applying a Calinski-Harabaz index obtains a value that suggests an optimal number of clusters by scoring each potential number of clusters 1020. In this case, the optimal number of clusters 1040 is eighteen based on the Calinksi-Harabaz index Other indices may alternatively be used. For example, the S-DBW index, the Xie-Beni index, or Silhouette indexes each are useful in identifying the optimal number of clusters. Generating a meaningful number of clusters allows the determination of related process features. For example, the individualized optimal number of burst clusters can lead to more reliable and valid burst-related features (e.g. average burst length) that better characterize an individual's writing and linguistic proficiency. In some embodiments, determining a desired number of clusters for an individual response may differ from individual to individual The optimal number of clusters, or burst clusters—tailored to an individual—suggest the level of fragmentation of one's writing process. High-scoring students likely to have less fragmented writing processes (and smaller numbers of clusters). High-scoring students will also exhibit more efficiency and strategy in managing their time than low-scoring students (having larger numbers of clusters). This information enables automatic generation of tailored feedback by a computer processor. This information can also be used as feedback for educator, students, and other people of interest, to improve the teaching and learning of writing.

Automated Scoring Based on Pause Features

In embodiments, IWI pause features (i.e., pauses between words) are analyzed using an automated scoring and feedback generation approach. It is noted, however, that in other embodiments, other pause features are analyzed using the automated scoring approach. These other pause features may include pauses between letters (i.e., inter-key intervals), pauses between phrases (i.e., inter-phrase intervals), and pauses between sentences (i.e., inter-sentence intervals), among others. It is further noted that although the 25 longest IWIs are considered in the example below, in other examples, a different number of pauses are analyzed. For example, in other examples, the 50 longest IWIs or 100 longest IWIs (among other numbers of IWIs) are analyzed. It is further noted that although the 25 longest IWIs are considered in the example below, in other examples, a different number of pauses are analyzed. For example, in other examples, the 50 longest IWIs or 100 longest IWIs (among other numbers of IWIs) are analyzed. Additionally, it is noted that information on other user actions (i.e., user actions other than pauses) may be analyzed using the automated scoring approach. In general, a vector including (i) data on types of actions performed by the user, (ii) time points associated with the actions, and (iii) locations associated with the actions may be generated and analyzed according to the automated scoring approaches described herein.

The relationship between IWI information and human scores can be evaluated and serve as a basis for feedback or score adjustment. Also, the association between IWI duration and median time-point combined with human scores can serve as a basis for feedback or score adjustment. That is, the correlation between information extracted from the writing processes in combination with an evaluation of the quality of the final product may be passed to, e.g., a scoring engine 210 and a rule engine 212. Automatic generation of scores based on IWI information is described in further detail above with reference to FIGS. 1 and 2A. As described above with reference to these figures, in embodiments, an electronic process log is received at a process log analyzer. The process log analyzer is configured to process the electronic process log to generate feature values related to the user's actions, and such feature values may include information on the M longest IWIs (e.g., 25 longest IWIs) associated with the constructed response. This information may include, for each of the M longest IWIs associated with the constructed response, (i) a duration of time of the IWI, and (ii) an associated time point, with the time point indicating a point in time at which the associated pause occurred (e.g., a median time point), among other information.

These feature values are received at a computer scoring engine that includes an automated scoring system configured to determine the score for the constructed response. The scoring engine may determine the score for the constructed response based on these feature values (and possibly other feature values, in some embodiments) and a scoring model (e.g., a statistical computer scoring model). In examples, the scoring model includes weighting factors for the feature values, with the weighting factors being determined based on a plurality of human-scored constructed responses (e.g., training texts). By applying the scoring model to the feature values, the score for the constructed response is determined.

To generate the scoring model used in the computer scoring engine, e.g. 210, the engine may receive the training texts with associated scores, e.g. training texts 214 may include associated scores. The engine or a model generation module 250 included therein uses the training texts to determine the weighting factors for the model, e.g., through a regression analysis. In an example, the weighting factors of the model may be determined via a machine learning application trained based on the training texts. Specifically, the machine learning application may utilize a linear regression analysis (e.g., a "leave-one-out" multiple linear regression, etc.), a logistic regression analysis, or another type of algorithm or analysis (e.g., a random forest learning analysis, decision tree analysis, random tree analysis, Classification And Regression Tree (CART) analysis, etc.). With the scoring model in place, the score for the constructed response may be determined by applying the scoring model to the feature values. Also, output from an assessment engine, e.g. 102, can be fed into a model generator 250, which may be part of a scoring engine, e.g. 210, or a separate and distinct process from a scoring engine, to continue training the scoring model.

In an embodiment, to generate weighting factors, e.g. weights 252, for the scoring model, leave-one-out multiple linear regression of human scores on the IWI vector (i.e., top 25 IWI durations and median time-points) was used, and the correlation coefficient of observed and predicted human scores was computed. It was hypothesized that there would be a moderate positive association between IWI information and human score because the processes indexed by the location and duration of the IWI should theoretically contribute to the quality of the final product. In addition to using all samples available for each essay task, to investigate whether there was a difference in association between IWI information and human scores between the clusters, the regression analyses were conducted separately for each cluster.

Ignoring cluster membership, the correlation coefficient between predicted and observed human scores was 0.46 for the policy recommendation essay (n=831) and 0.48 for the argumentation essay (n=902). However, when cluster membership was taken into account, notable differences were found between the clusters. The cluster-specific regression models resulted in correlation coefficients of 0.47 for cluster 1 and 0.65 for cluster 2 for the policy recommendation essay. Similar results were observed for the argumentation essay, where cluster 1 also yielded a considerably lower correlation coefficient (0.46) than cluster 2 (0.51).

Discussion

The above-described analysis focused on the 25 longest inter-word pauses in each essay and indicated that student response patterns fell into two major groups. In pattern 1, the 25 longest pauses were distributed relatively evenly throughout the composition. Essays that exemplify pattern 1 received higher mean human scores, contained more words, and were composed over a longer active writing time. In pattern 2, the longest 25 pauses were somewhat shorter than in pattern 1, and were concentrated at the beginning and end of the composition. Essays that exemplify pattern 2 received lower mean human scores, had fewer words, and were written over a shorter active composition time. These findings were replicated across two writing prompts, each focused on a different writing purpose and administered to different student samples. It is worth noting that the results of writing patterns should be interpreted at the group level; that is, the patterns do not reflect the distribution of the 25 longest IWIs of any individual electronic process log.

Pauses of more than two seconds may be described as terminating "bursts" of text production, and tend to be interpreted in think-aloud protocols as occasions for sentence-level planning. This cognitive interpretation can readily be applied to pattern 1. As can be observed in FIGS. 8A-10, the longest pauses produced by pattern-1 writers fell most often between 1.5 and 4 seconds in duration, typical of pauses between bursts. This interpretation is strengthened by the fact that pattern-1 pauses were evenly distributed across the entire text. The resulting rhythm—a regular series of bursts of fast production delimited by pauses of 2 seconds or more—may be emblematic of fluent text production, in which the writer pauses primarily to plan the next major grammatical or textual unit.

The striking feature of pattern 2 is the presence of a second kind of pause, mostly shorter than the pauses observed in pattern 1, concentrated near the beginning and the end of the composition. These time points are arguably where a writer who has difficulty generating text is most likely to experience difficulty. This is consistent with the notion that certain kinds of behavioral events, such as text production followed by revision, are associated with shorter pauses. It is thus possible, though by no means certain, that the higher frequency of short pauses concentrated at the beginning and ends of pattern 2 essays reflects difficulties in text generation, leading to false starts and interruptions instead of fluent text production at the beginning of an essay (when the writer is under the most stress to plan content), and at the end of an essay (when the writer may be running out of ideas, and thus once more experiencing higher levels of uncertainty about what to write next.) A post-hoc qualitative analysis of a small subset of logs from this dataset was conducted, and it was found that some weaker writers did produce a small amount of text—a few words, or even part of a word—and then delete it after a short pause, only to proceed to another false start. It is thus possible that pattern 2 involves this kind of hesitation, although it cannot be confirmed without further analysis in which the distribution of IWIs is correlated with the distribution of deletions and edits.

Under the approaches of the instant application, a new method of comparing temporal sequences of IWIs across different students using a vector representation is utilized. This approach enables global patterns in pausing behavior to be described, which may correspond to different cognitive strategies or styles of writing. It is noted that aspects of the approaches described herein may vary in embodiments. For example, in other embodiments, a different scale transformation (e.g., on the IWI time-point) may be used. Further, in other examples, other similarity measures (e.g., Euclidean or Mahalanobis types of distance measures) and other representations such as matched filtering may be used. Further, although approaches described herein analyzed the M longest IWIs associated with a constructed response, in other examples, all IWIs may be analyzed, as this may provide more information than a subset of the IWIs. In other examples, the representation may be enriched to include information about the context of writing actions such as IWI. For example, some IWIs happen between words in a long burst of text production; others, in the context of other actions, such as edits or deletions. The second cluster, in which most pauses were near the beginning and end of student essays, may be interpreted differently if they were associated with editing and deletion, than if they were associated with uninterrupted text production. Thus, in embodiments, analyses that identify qualitative, linguistic or behavioral differences may be undertaken, thus allowing those findings to be related to the differences in writing patterns described here.

Figure 11A:
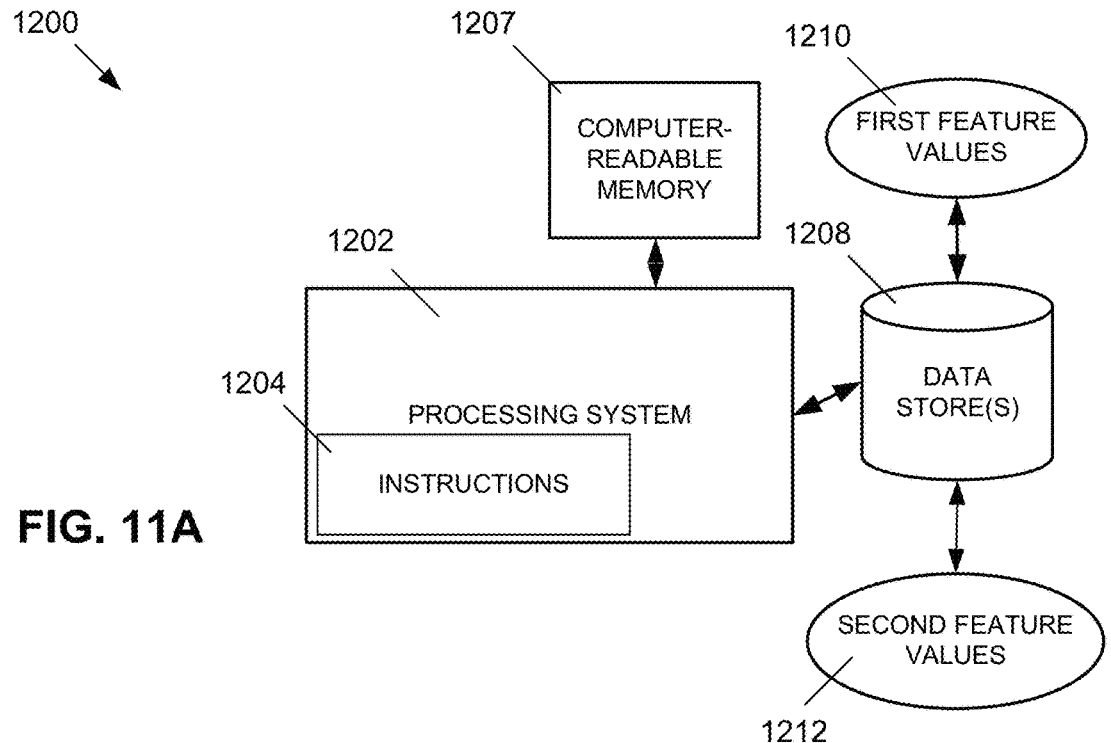
FIG. 11A depicts an exemplary system including a stand-alone computer architecture in accordance with disclosed embodiments.
Figure 11B:
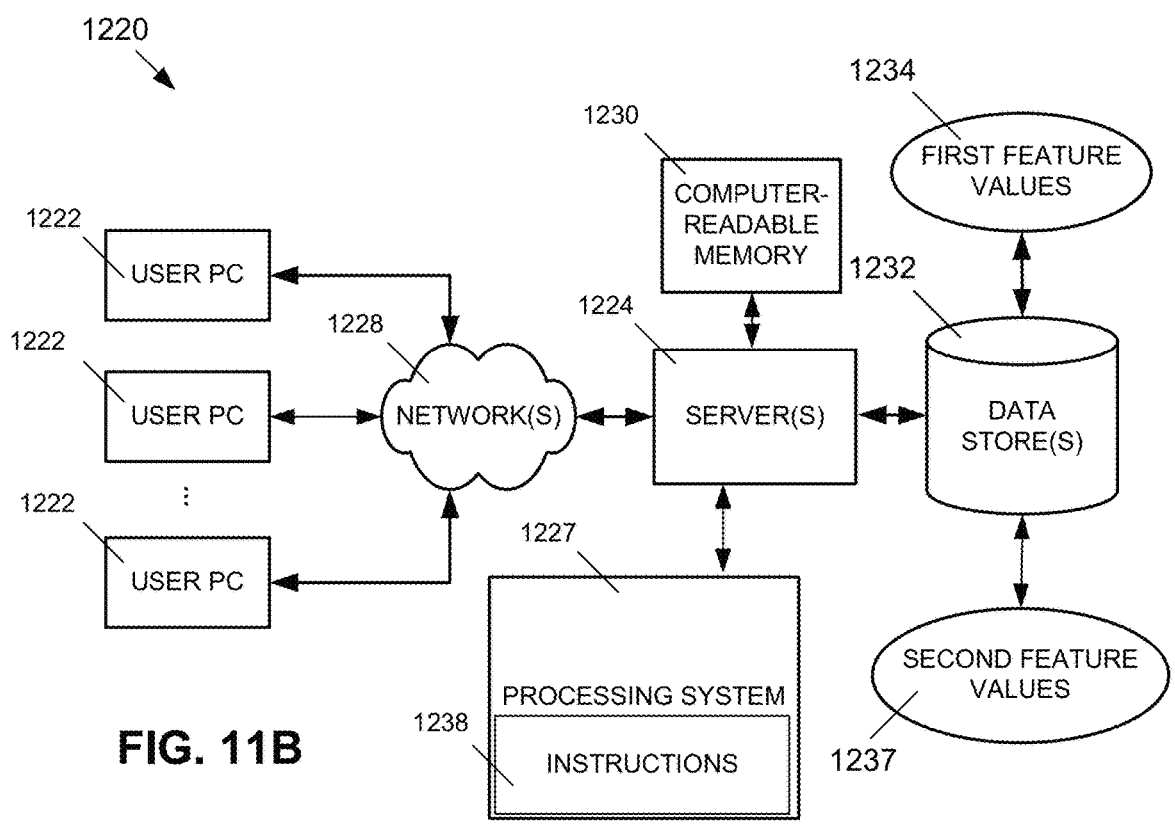
FIG. 11B depicts an exemplary system including a client server architecture in accordance with disclosed embodiments.
Figure 11C:
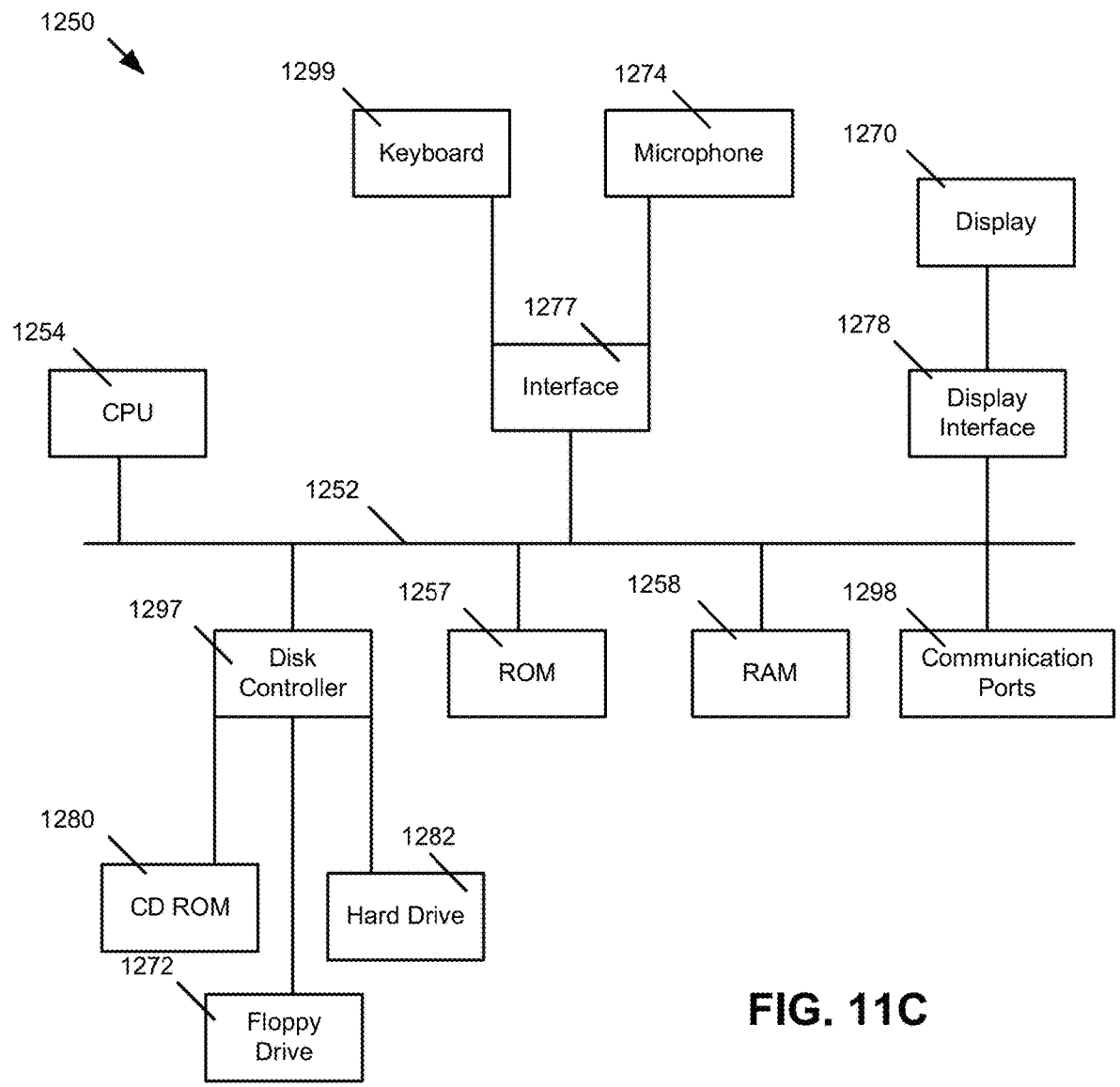
FIG. 11C depicts a block diagram of exemplary hardware in accordance with disclosed embodiments.

FIGS. 11A, 11B, and 11C depict example systems for scoring a constructed response generated by a user and providing information on the user's writing behavior. For example, FIG. 11A depicts an exemplary system 1200 that includes a standalone computer architecture where a processing system 1202 (e.g., one or more computer processors located in a given computer or in multiple computers that may be separate and distinct from one another) includes instructions 1204 for scoring a constructed response generated by a user and providing information on the user's writing behavior. The processing system 1202 has access to a computer-readable memory 1207 in addition to one or more data stores 1208. The one or more data stores 1208 may include first feature values 1210 as well as second feature values 1212. The processing system 1202 may be a distributed parallel computing environment, which may be used to handle very large-scale data sets.

FIG. 11B depicts a system 1220 that includes a client-server architecture. One or more user PCs 1222 access one or more servers 1224 executing instructions 1238 for scoring a constructed response generated by a user and providing information on the user's writing behavior on a processing system 1227 via one or more networks 1228. The one or more servers 1224 may access a computer-readable memory 1230 as well as one or more data stores 1232. The one or more data stores 1232 may contain first feature values 1234 as well as second feature values 1237.

FIG. 11C shows a block diagram of exemplary hardware for a standalone computer architecture 1250, such as the architecture depicted in FIG. 11A that may be used to contain and/or implement the program instructions of system embodiments of the present disclosure. A bus 1252 may serve as the information highway interconnecting the other illustrated components of the hardware. A processing system 1254 labeled CPU (central processing unit) (e.g., one or more computer processors at a given computer or at multiple computers), may perform calculations and logic operations required to execute a program. A non-transitory processor-readable storage medium, such as read only memory (ROM) 1257 and random access memory (RAM) 1258, may be in communication with the processing system 1254 and may contain one or more programming instructions for performing the method for scoring a constructed response generated by a user and providing information on the user's writing behavior. Optionally, program instructions may be stored on a non-transitory computer-readable storage medium such as a magnetic disk, optical disk, recordable memory device, flash memory, or other physical storage medium.

In FIGS. 11A, 11B, and 11C, computer readable memories 1207, 1230, 1257, 1258 or data stores 1208, 1232, 1257, 1258, 1272, 1280, 1282 may include one or more data structures for storing and associating various data used in the example systems for scoring a constructed response generated by a user and providing information on the user's writing behavior. For example, a data structure stored in any of the aforementioned locations may be used to associate feature values and rules of a rule engine. Other aspects of the example systems for scoring a constructed response generated by a user and providing information on the user's writing behavior may be stored and associated in the one or more data structures.

A disk controller 1297 interfaces one or more optional disk drives to the system bus 1252. These disk drives may be external or internal floppy disk drives such as 1272, external or internal CD-ROM, CD-R, CD-RW or DVD drives such as 1280, or external or internal hard drives 1282. As indicated previously, these various disk drives and disk controllers are optional devices.

Each of the element managers, real-time data buffer, conveyors, file input processor, database index shared access memory loader, reference data buffer and data managers may include a software application stored in one or more of the disk drives connected to the disk controller 1297, the ROM 1257 and/or the RAM 1258. The processor 1254 may access one or more components as required.

A display interface 1278 may permit information from the bus 1252 to be displayed on a display 1270 in audio, graphic, or alphanumeric format. Communication with external devices may optionally occur using various communication ports 1298.

In addition to these computer-type components, the hardware may also include data input devices, such as a keyboard 1299, or other input device 1274, such as a microphone, remote control, pointer, mouse and/or joystick.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein and may be provided in any suitable language such as C, C++, JAVA, for example, or any other suitable programming language. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

It is claimed:

1. A computer-implemented method for automatically providing feedback on the writing behavior of a user when generating an evaluation response written via a graphical-user interface displayed on a computing device, the method comprising:

generating, using a scoring system, a score for the evaluation response using first feature values derived from the evaluation response;

receiving an electronic process log associated with the evaluation response that comprises second feature values derived from the evaluation response, the second feature values comprising a plurality of time-stamped entries, each of the entries being associated with and corresponding actions taken in writing the evaluation response in the graphical user interface and characterize planning, revising, and editing by a user;

processing the electronic process log with the processing system to generate a vector having a predetermined number of vector elements containing information related to actions taken in writing the evaluation response in the graphical user interface;

generating feedback to the evaluation response based on the vector providing diagnostic feedback to the user characterizing the behavior of the user when writing the evaluation response; and providing, in combination, the score for the evaluation response with the feedback to the evaluation response;

wherein the processing further includes comparing the vector with one or more other vectors each associated with other evaluation responses and generating, using at least one similarity measure, clusters of responses including the evaluation response and the other evaluation responses, wherein clusters are generated based in part on closeness of the vector associated with the evaluation response to the vectors associated with the other evaluation responses;

wherein the actions include pauses occurring during the writing of the evaluation response that are indicative of the behavior of the user while generating the evaluation response, and wherein the vector elements further include durations of time elements indicating how long the user paused between typing adjacent words, letters, phrases, sentences, or paragraphs of the evaluation response as well as location information identifying where the pauses occurred within the response.

2. The computer-implemented method of claim 1, wherein processing the electronic process log further comprises applying a clustering function to generate an optimal number of burst-clusters indicating periods during which the user student generated text for distinct periods of time; and generating distinct statistics based on (i) within cluster information and (ii) between cluster information; and including the distinct statistics within the vector.

3. The computer implemented method of claim 2, wherein the keystrokes are associated with text that is included in the evaluation response and deleted text entered when writing the evaluation response in the graphical user interface but deleted before submitting the evaluation response.

4. The computer-implemented method of claim 1, wherein the vector elements include:
data indicating types of actions performed by a user when generating the evaluation response; and
time points associated with each action.

5. The computer-implemented method of claim 4, wherein the vector elements also include:
locations associated with each action, each location indicating whether a respective action occurred within a word, between words, within a phrase, between phrases, within a sentence, between sentences, within a paragraph, or between paragraphs; or
duration information regarding the duration of a period of time during which an action was performed.

6. The computer-implemented method of claim 1, wherein processing further includes comparing the vector with one or more other vectors each associated with other evaluation responses.

7. The computer-implemented method of claim 1, wherein processing further includes applying a scoring model to the vector, the scoring model comprising weights determined in association with more training texts.

8. The computer-implemented method of claim 1, wherein generating feedback is further based on the evaluation response or an assessment of the evaluation response.

9. The computer-implemented method of claim 1, wherein the scoring system utilizes a machine learning model trained using a plurality of historical human-scored responses.

10. A system for providing feedback to an evaluation response, the system comprising:
a processing system; and
computer-readable memory in communication with the processing system encoded with instructions for commanding the processing system to execute steps comprising:
receiving an electronic process log for associated with the evaluation response that comprises a plurality of time-stamped entries, each of the entries being associated with actions taken in writing the response;
processing the electronic process log with the processing system to generate a vector having a predetermined number of vector elements containing information related to actions taken in writing the evaluation response in the graphical user interface, the vector elements comprises longest inter-word-intervals (IWIs), each IWI comprising (i) a duration of time of the IWI and (ii) an associated time point at which an associated pause occurred; and
generating feedback to the writing the evaluation response in the graphical user interface based on the vector;
wherein processing further includes comparing the vector with one or more other vectors each associated with other evaluation responses and generating, using at least one similarity measure, clusters of responses including the evaluation response and the other evaluation responses, wherein clusters are generated based in part on closeness of the vector associated with the evaluation response to the vectors associated with the other evaluation responses;
wherein the at least one similarity measure is selected from a group consisting of: a cosine similarity measure, a Euclidean similarity measure, or a Mahalanobis similarity measure;
wherein the pauses forming part of the Ms comprise pauses occurring during the writing of the evaluation response that are indicative of the behavior of the user while generating the evaluation response, and wherein the vector elements further include durations of time elements indicating how long the user paused between typing adjacent words, letters, phrases, sentences, or paragraphs of the evaluation response as well as location information identifying where the pauses occurred within the response.

11. The system of claim 10, wherein actions taken in writing the evaluation response in the graphical user interface include keystrokes made by a user in generating the written response and indicating a change in text of the written response.

12. The system of claim 11, wherein the keystrokes are associated with text that is included in the written response and deleted text entered when writing the evaluation response in the graphical user interface but deleted before submitting the evaluation response.

13. The system of claim 10, wherein actions include pauses, and wherein the vector further includes durations of time elements indicating how long the user paused between typing adjacent words, letters, phrases, sentences, or paragraphs of the evaluation response.

14. The system of claim 10, wherein the vector elements include:
   data indicating types of actions performed by a user when generating the evaluation response; and
   time points associated with each action.

15. The system of claim 14, wherein the vector elements also include:
   locations associated with each action, each location indicating whether a respective action occurred within a word, between words, within a phrase, between phrases, within a sentence, between sentences, within a paragraph, or between paragraphs.

16. The system of claim 10, wherein generating feedback is further based on the evaluation response or an assessment of the evaluation response.

17. The system of claim 10, wherein processing further includes applying a scoring model to the vector, the scoring model comprising weights determined in association with more training texts.

18. The system of claim 10, wherein the generating utilizes a machine learning model trained using a plurality of historical human-scored responses.

19. A non-transitory computer-readable storage medium for providing automatic feedback to an evaluation response, the computer-readable storage medium comprising computer executable instructions which, when executed, cause a processing system to execute steps including:
   receiving an electronic process log for associated with the evaluation response that comprises a plurality of time-stamped entries, each of the entries being associated with actions taken in writing the evaluation response in the graphical user interface;
   processing the electronic process log with the processing system to generate a vector having a predetermined number of vector elements containing information related to actions taken in writing the evaluation response in the graphical user interface; and
   generating, by inputting the evaluation response into a scoring system and the vector into a machine learning model trained using a plurality of historical human-scored responses, a score for the evaluation response based on an output of the scoring system as well as feedback to the evaluation response based on an output of the machine learning model;
   wherein the vector comprises each of the following:
      (i) data indicating types of actions performed by a user in generating the written response;
      (ii) time points associated with the actions, each time point indicating a point in time in the composition process at which an associated action occurred;
      (iii) locations associated with the actions, each location indicating whether an associated action occurred within a word, between words, within a phrase, between phrases, within a sentence, between sentences, within a paragraph, or between paragraph; and
      (iv) duration of the action in terms of the time elapsed or text length;
   wherein processing further includes comparing the vector with one or more other vectors each associated with other evaluation responses and generating, using at least one similarity measure, clusters of responses including the evaluation response and the other evaluation responses, wherein clusters are generated based in part on closeness of the vector associated with the evaluation response to the vectors associated with the other evaluation responses.

* * * * *